(12) United States Patent
Tsuyuki et al.

(10) Patent No.: US 11,399,795 B2
(45) Date of Patent: Aug. 2, 2022

(54) X-RAY CT APPARATUS AND IMAGING CONTROL METHOD

(71) Applicant: Canon Medical Systems Corporation, Otawara (JP)

(72) Inventors: Masaharu Tsuyuki, Nasushiobara (JP); Takahiro Yoda, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 52 days.

(21) Appl. No.: 16/920,910

(22) Filed: Jul. 6, 2020

(65) Prior Publication Data
US 2021/0007699 A1    Jan. 14, 2021

(30) Foreign Application Priority Data

Jul. 9, 2019   (JP) .............................. JP2019-127767
Jun. 30, 2020  (JP) .............................. JP2020-112694

(51) Int. Cl.
*A61B 6/00*   (2006.01)
*A61B 6/02*   (2006.01)
*A61B 6/03*   (2006.01)

(52) U.S. Cl.
CPC .............. *A61B 6/545* (2013.01); *A61B 6/027* (2013.01); *A61B 6/035* (2013.01); *A61B 6/4085* (2013.01)

(58) Field of Classification Search
CPC ...... A61B 6/0275; A61B 6/035; A61B 6/4085
See application file for complete search history.

(56) References Cited

U.S. PATENT DOCUMENTS

2015/0327825 A1*  11/2015  Suzuki ................... A61B 6/035
                                                      378/4

FOREIGN PATENT DOCUMENTS

JP         2002-306468         10/2002

* cited by examiner

*Primary Examiner* — Dani Fox
(74) *Attorney, Agent, or Firm* — Oblon, McClelland, Maier & Neustadt, L.L.P.

(57) ABSTRACT

According to one embodiment, an X-ray computed tomography (CT) apparatus includes an X-ray tube, an area detector, a rotary frame, generation circuitry, processing circuitry, and a controller. The generation circuitry is configured to generate a reference image of the subject based on an output from the area detector that is given in response to radiation of the X-rays from a predetermined position around the rotational axis for a period required to perform on/off control of radiation of the X-rays. The processing circuitry is configured to set, based on the reference image, an imaging condition for use in scanning for the subject. The controller is configured to control the scanning based on the set imaging condition.

14 Claims, 14 Drawing Sheets

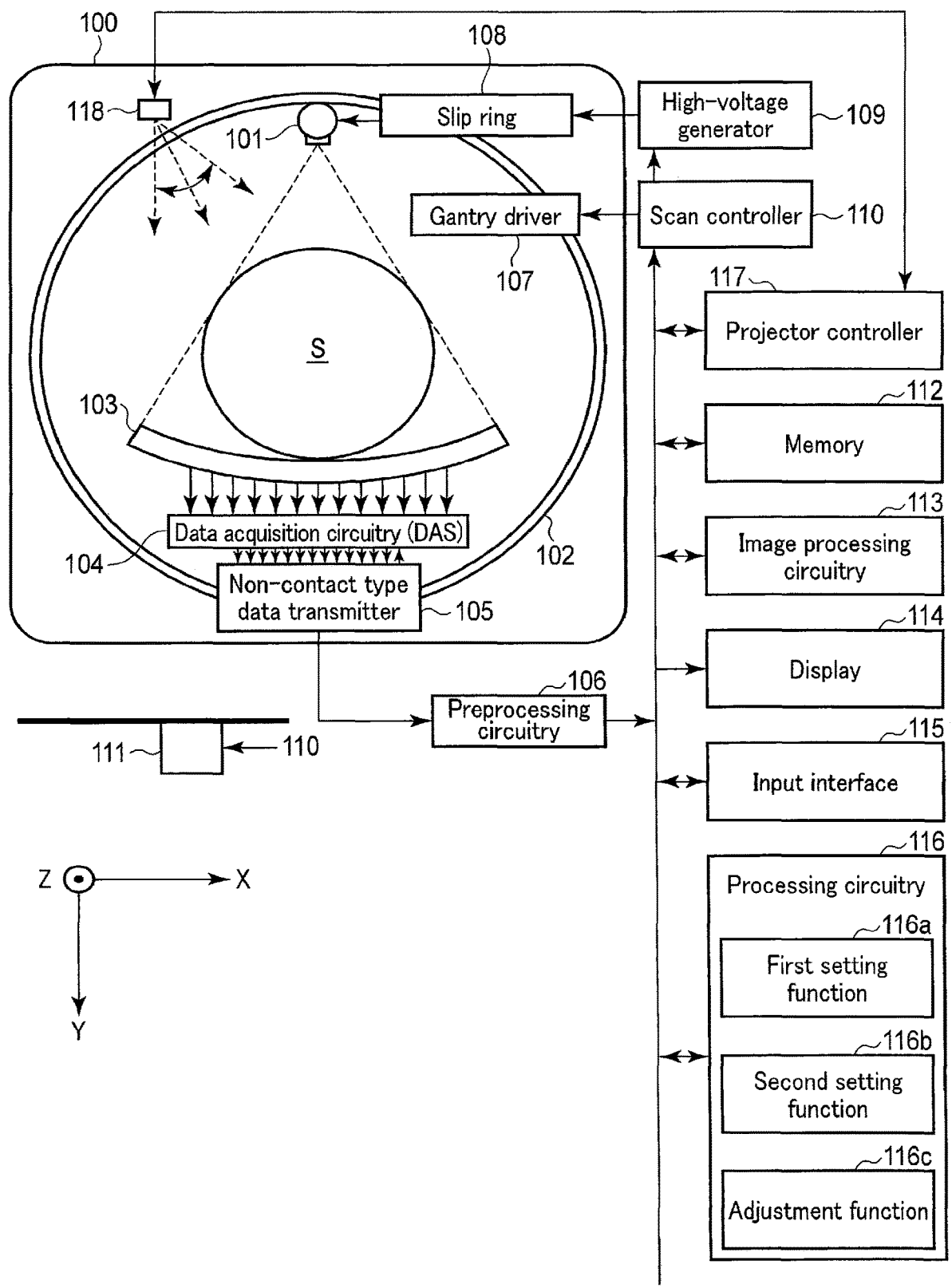
F I G. 1

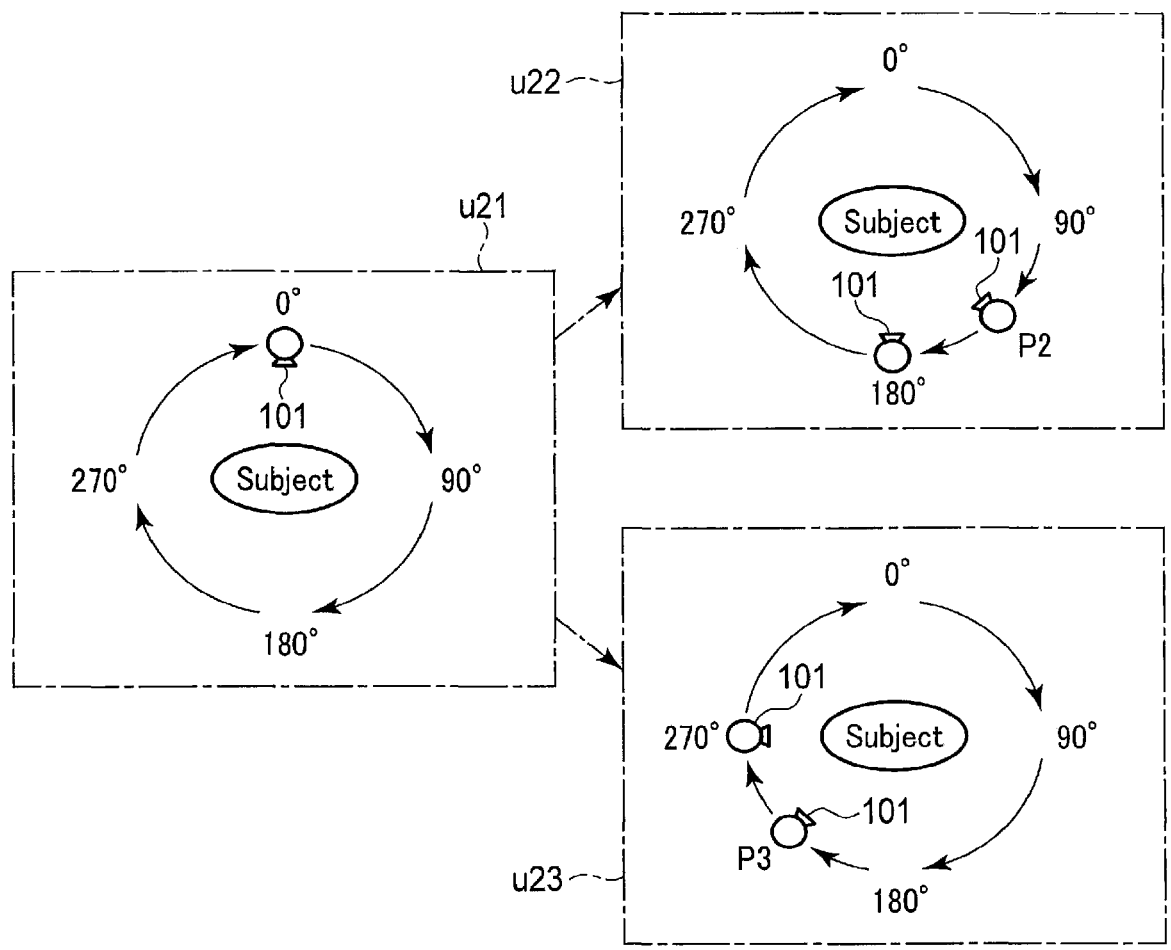
F I G. 6

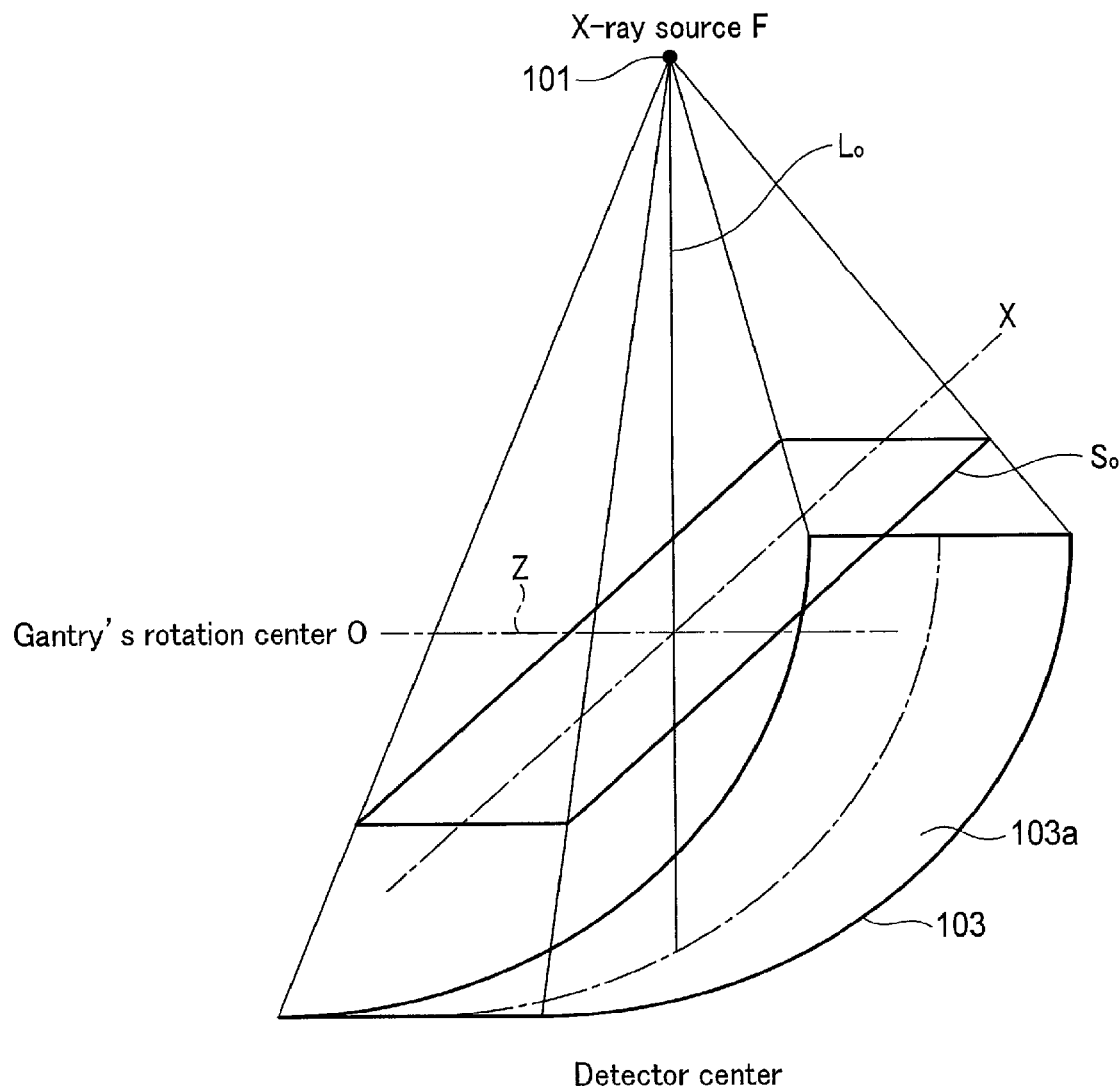
F I G. 12

X-RAY CT APPARATUS AND IMAGING CONTROL METHOD

CROSS-REFERENCE TO RELATED APPLICATIONS

This application is based upon and claims the benefit of priority from prior Japanese Patent Applications No. 2019-127767, filed Jul. 9, 2019, and No. 2020-112694, filed Jun. 30, 2020, the entire contents of all of which are incorporated herein by reference.

FIELD

Embodiments described herein relate generally to an X-ray computed tomography (CT) apparatus and an imaging control method.

BACKGROUND

Examinations with an X-ray CT apparatus generally adopt the combination of a preceding operational step of performing X-ray irradiation for acquiring data for a reference image and a subsequent operational step of performing CT imaging (scanning) under the scanning conditions determined based on the reference image. In such a combination, as one example, scanogram imaging is performed in advance of the scanning so that a two-dimensional X-ray fluoroscopic image (may also be called "scanogram" below) for use in positioning is obtained as the reference image.

The scanogram imaging is performed without rotation of a gantry having an X-ray tube, but performed while a couch is driven. In some instances, the scanogram imaging may be performed using X-ray irradiation in multiple directions such as the front direction and the side direction of a subject placed on the couch. For example, to perform the scanogram imaging in the front direction, an X-ray tube is arranged at the 0° position that squarely faces the subject, and the X-ray tube is caused to radiate X-rays toward the subject while the couch is driven and moved. To perform the scanogram imaging in the side direction, the X-ray tube is arranged at the lateral side position with respect to the subject (90° position), and the X-ray tube is caused to radiate X-rays toward the subject while the couch is driven and moved. For the scanogram imaging in multiple directions, either the X-ray irradiation in the front direction or the x-ray irradiation in the side direction may be performed first.

One or more scanograms are thus obtained from the scanogram imaging in one direction or the scanogram imaging in multiple directions. After the scanogram imaging, imaging (scanning) conditions are set based on the one or more scanograms, the couch is moved, and rotation of the gantry is initiated. Then, tomograms are obtained based on data acquired by the scanning.

The X-ray CT apparatus adapted for operations as above normally serves well. However, the study of the present inventors has revealed that such an X-ray CT apparatus requires time to proceed with the data acquisition by X-ray irradiation as the preceding operational step in said combination, in which the reference image obtained in the preceding operational step is used for determining the scanning conditions for the subsequent scanning step. The present inventors thus see room for improvement in this respect. For example, the scanogram imaging as above must drive and move the couch, and as such, it takes time depending on the distance traveled by the couch.

BRIEF DESCRIPTION OF THE DRAWINGS

FIG. 1 is a schematic diagram showing an exemplary configuration of an X-ray CT apparatus according to a first embodiment.

FIG. 6 includes schematic diagrams for explaining another modification of the certain operation according to the embodiment.

FIG. 12 is a schematic diagram for explaining a certain operation of an X-ray CT apparatus according to a seventh embodiment.

DETAILED DESCRIPTION

Figure 2:
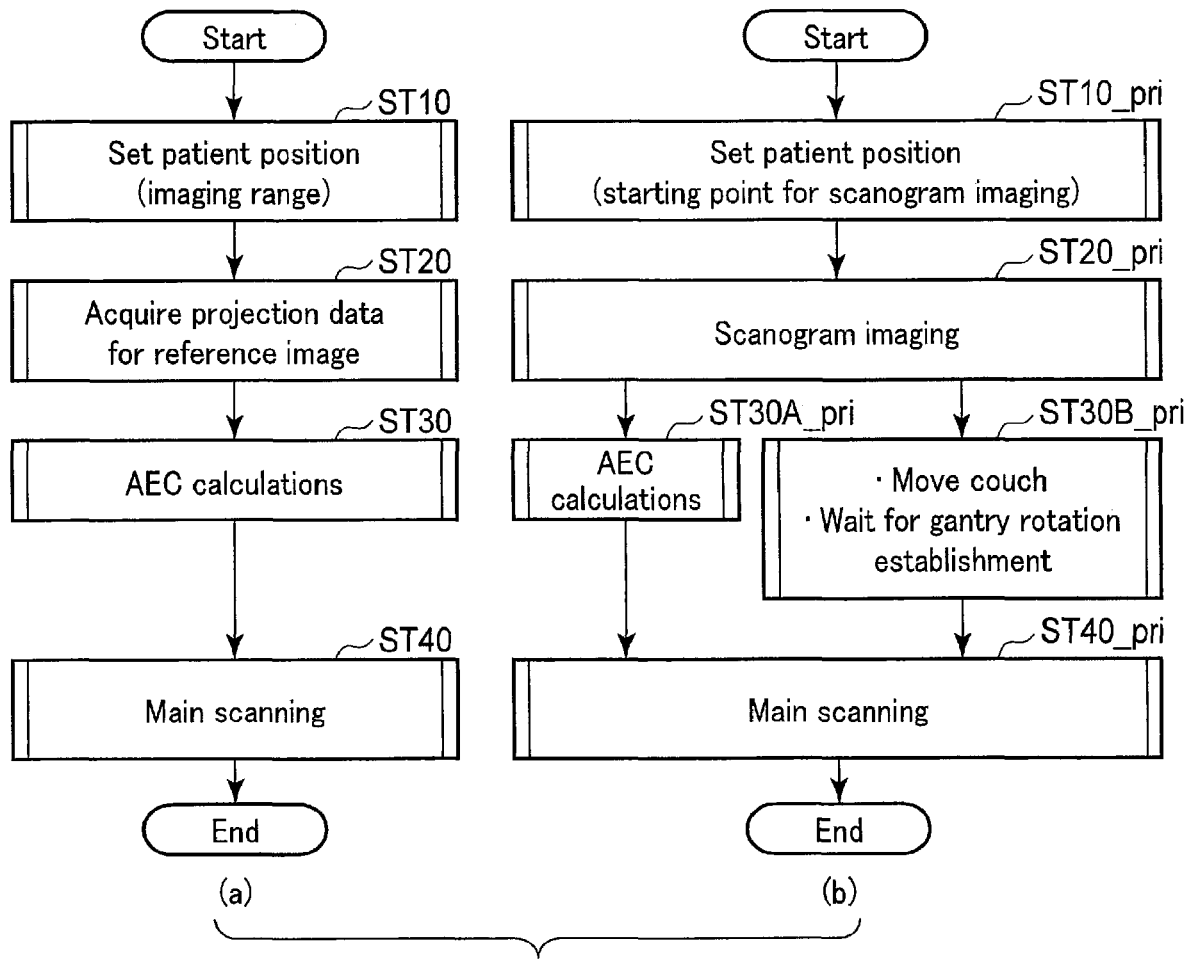
FIG. 2 includes flowcharts for explaining an operational sequence according to the embodiment in comparison with the conventional operational sequence.

According to one embodiment, an X-ray computed tomography (CT) apparatus includes an X-ray tube, an area detector, a rotary frame, generation circuitry, processing circuitry, and a controller. The X-ray tube is configured to radiate cone beam-shaped X-rays. The area detector is configured to detect the X-rays having radiated from the X-ray tube and passed through a subject. The rotary frame supports the X-ray tube and the area detector in such a manner that the X-ray tube and the area detector are rotatable about a rotational axis. The generation circuitry is configured to generate a reference image of the subject based on an output from the area detector that is given in response to radiation of the X-rays from a predetermined position around the rotational axis for a period required to perform on/off control of radiation of the X-rays. The processing circuitry is configured to set, based on the reference image, an imaging condition for use in scanning for the subject. The controller is configured to control the scanning based on the set imaging condition.

Therefore, the reference image can be obtained without a couch movement, and the setup time up to the scanning can also be shortened.

Now, the embodiments will be described with reference to the drawings. By way of example, each embodiment will be described assuming that the corresponding X-ray CT apparatus employs a movable couch top for placement of a subject, but the embodiments are not limited to such a type. Each embodiment is likewise applicable to any types of X-ray CT apparatuses including, for example, an X-ray CT apparatus employing a gantry adapted for automatic movement, an upright CT apparatus, etc.

First Embodiment

FIG. 1 is a schematic diagram showing an exemplary configuration of an X-ray CT apparatus according to the first embodiment. This X-ray CT apparatus includes a gantry 100. The gantry 100 is constituted by a main frame. The main frame is formed of metal such as aluminum or the like. The main frame has a bore at its center. The main frame supports a rotary frame 102 at its periphery so that the rotary frame 10 can rotate about a rotational axis (i.e., the subject's body axis). More specifically, the frame periphery and the rotary frame 102 are connected with each other via bearings. The rotary frame 102 retains an X-ray tube unit 101 and an X-ray detector 103 so that they face each other and they can rotate about the rotational axis. The rotary frame 102 is driven by a gantry driver 107 to rotate about the rotational axis. Note that the X-ray CT apparatus according to the embodiment may be designed as a double-tube type apparatus where two pairs of an X-ray tube unit and an X-ray detector are mounted on the rotary frame. In that case, the line connecting the X-ray tube unit to the X-ray detector of the first pair and the line connecting the X-ray tube unit to the X-ray detector of the second pair may intersect at approximately 90°. For explanation of the embodiment, the description will basically assume the X-ray CT apparatus to be a single-tube type. At the scanning step, a subject placed on a top (couch top) of a couch unit 111 is interposed between the X-ray tube unit 101 and the X-ray detector 103. The couch top is adapted for forward and backward movement along its longitudinal direction by a non-illustrated driver provided in the couch unit 111.

The X-ray tube unit 101 is adapted to generate X-rays upon receiving a tube-voltage application and a filament-current supply via a slip ring 108 from a high-voltage generator 109, and to emit (radiate) the X-rays from an X-ray focal point. The X-rays radiated from the X-ray focal point are shaped into, for example, a cone beam (pyramid shape) by a non-illustrated wedge and slit furnished at the X-ray radiating window of the X-ray tube unit 101. The wedge is a filter for exposure reduction, and the slit is a gap for beam shaping. The X-ray tube unit 101 with such a configuration serves as an X-ray tube for radiating cone beam-shaped X-rays. FIG. 1 shows the radiation range of the X-rays using dashed lines. Also, the description assumes a Z-axis to be an axis defined in concordance with the rotational axis of the rotary frame 102. A Y-axis is an axis orthogonal to the Z-axis and defined in concordance with a line connecting the X-ray focal point of the X-ray tube unit 101 to the center of a detection plane of the X-ray detector 103. An X-axis is an axis orthogonal to both the Y-axis and the Z-axis. As such, the X-Y-Z orthogonal coordinate system is a rotating coordinate system that is rotated following the rotation of the X-ray tube unit 101.

The X-ray detector 103 includes multiple X-ray detecting elements each adapted to detect X-rays having passed through the subject and output an electric signal reflecting the dose of the incident X-rays. There are two major techniques available for converting the incident X-rays into electric charges, namely, a technique utilizing an indirect-conversion type mechanism and a technique utilizing a direct-conversion type mechanism. The indirect-conversion type refers to the technique of converting X-rays into light using a fluorescent component such as a scintillator, and further converting the light into electric charges using a photoelectric converter such as a photodiode. The direct-conversion type refers to the technique based on generation of an electron-hole pair in the semiconductor and its transfer to an electrode, that is, the photo-conductive phenomenon caused by X-rays. The X-ray detecting elements may adopt either of such techniques, and the description here will assume that the X-ray detecting elements adopt the former technique, i.e., the one utilizing the indirect-conversion type mechanism. Also, the X-ray detecting elements are arranged in a grid pattern with channels orthogonal to the rotational axis and rows along the rotational axis, and they may be arranged, for example, two-dimensionally in 320 rows×912 channels. The X-ray detector 103 adapted as above serves as an area detector for detecting X-rays having been radiated from the X-ray tube and passed through the subject. To put it another way, the X-ray CT apparatus according to the embodiment may be an area-detector CT (ADCT) apparatus with an area detector, and adapted to perform volume scanning.

Data acquisition circuitry 104 is provided, which may be called a data acquisition system (DAS). The data acquisition circuitry 104 includes an IV converter, an integrator, an amplifier, and an analog-to-digital converter (ADC) for each channel of the X-ray detector 103. The IV converter is adapted to convert an electric signal on the corresponding channel of the X-ray detector 103 into a voltage. The integrator is adapted to periodically integrate voltage signals output from the IV converter, in synchronization with the X-ray radiation cycles. The amplifier is adapted to amplify a signal output from the integrator. The ADC is adapted to convert a signal output from the amplifier into a digital signal. In this manner, the data acquisition circuitry 104 acquires the signals output from the X-ray detector 103 and convert them into digital signals (may also be called "pure raw data"). The data acquisition circuitry 104 is further adapted to send this pure raw data to preprocessing circuitry 106 via a non-contact type data transmitter 105 that uses a magnetic or optical transmission and reception technique. The preprocessing circuitry 106 is adapted to subject the pure raw data to processing such as sensitivity correction, logarithmic conversion, etc., so as to generate projection data. The projection data is then stored in a memory 112.

A scan controller 110 is provided, which is adapted to control operations of the data acquisition circuitry 104, the gantry driver 107, the high-voltage generator 109, the couch unit 111, etc., in order to perform scanning according to set imaging conditions. The scanning here is intended to be performed after determining and setting the imaging conditions based on the projection data acquired by switching on and off the radiation of X-rays, e.g., using pulsed X-rays, to realize a reduced X-ray irradiation time as will be described later. The scanning may be either non-helical scanning or helical scanning. For the present embodiment, the description will assume exemplary instances where the scanning is non-helical scanning. The scan controller 110 has, for example, a first control function and a second control function. The scan controller 110 may have a third control function instead of the second control function. The scan controller 110 is also adapted to perform control so that the data acquisition for obtaining a reference image uses radiation of X-rays that produces a reduced dose as compared to the scanning.

More specifically, the first control function is a function to control the scanning based on the set imaging conditions. This first control function may include, for example, performing control for suspending radiation of X-rays and continuing rotation of the rotary frame 102 for the period after completion of the X-ray irradiation for generating the reference image and until start of the scanning. Note that the term "reference image" here may be replaced with "fluoroscopic image" or "image for use in positioning".

The second control function is a function to control the X-ray tube unit 101 to radiate X-rays using, as a predetermined position, either the 0° position at the top of the trajectory around the rotational axis or the 180° position at the bottom of the trajectory, whichever is closer to the position of the X-ray tube unit 101 on the trajectory at the time that an instruction to start taking the reference image is given.

The third control function is a function to control the X-ray tube unit 101 to radiate X-rays using, as the predetermined position, either the 90° position or the 270° position at the respective midpoint between the top and bottom of the trajectory around the rotational axis, whichever is closer to the position of the X-ray tube unit 101 on the trajectory at the time that the instruction to start taking the reference image is given.

The memory 112 is adapted to store various data including, for example, image data such as projection data, reference image data, volume data, and tomogram data, programs for later-described processing circuitry 116 to read and execute, data under processing by the processing circuitry 116, and results of processing. Such a memory 112 is constituted by a memory main component for storing electric information, such as a hard disk drive (HDD), etc., as well as peripheral circuitry pertaining to the memory main component, such as a memory controller, a memory interface, etc.

Image processing circuitry 113 is provided, which is adapted to generate, in the course of obtaining the reference image, reference image data based on the projection data stored in the memory 112. When, for example, the on/off control of X-rays is not very smooth, and the on/off control of X-ray irradiation in one-view units is not enabled, the image processing circuitry 113 generates the reference image data by summing up the set of projection data for multiple views that form an on/off controllable unit, as long as a blur does not stand out. When the on/off control of X-ray irradiation in one-view units is possible, the projection data for one view is adopted as the reference image data. Such image processing circuitry 113 constitutes generation circuitry adapted to generate the reference image of a subject based on the output from the X-ray detector 103 that is given in response to the radiation of X-rays from the predetermined position around the rotational axis for as long period as required to perform the on/off control of the radiation. For example, this generation circuitry generates the reference image based on the output from the area detector given in response to the radiation of X-rays from the predetermined position during ongoing rotation of the rotary frame 102. Besides, the generation circuitry constituted by the image processing circuitry 113 is not limited to such a configuration, and the image processing circuitry 113 may also constitute generation circuitry adapted to generate the reference image of the subject based on the output from the X-ray detector 103 that is given in response to the radiation of X-rays from the predetermined position around the rotational axis during rotation of the rotary frame 102 for a period that would allow for obtaining one fluoroscopic image. Or, the image processing circuitry 113 may constitute generation circuitry adapted to generate the reference image of the subject based on the output from the X-ray detector 103 that is given in response to the radiation of X-rays from the predetermined position around the rotational axis during rotation of the rotary frame 102 for a period corresponding to one or more views. When a fluoroscopic image from the projection data is found to include a distortion, the image processing circuitry 113 may generate the reference image data indicative of a distortion-corrected fluoroscopic image through reprojection processing of reprojecting onto a flat plane.

The image processing circuitry 113 is also adapted to reconstruct volume data based on the projection data stored in the memory 112 when the scanning is performed. The volume data is stored in the memory 112. The image processing circuitry 113 is further adapted to generate tomogram data based on the volume data stored in the memory 112, for a tomogram of the subject to be displayed. The tomogram data is stored in the memory 112.

A display 114 is provided, which includes a display main component for displaying medical images, etc. based on the data in the memory 112, internal circuitry for supplying display signals to the display main component, and peripheral circuitry including connectors, cables, or the like for connection between the display main component and the internal circuitry. The display 114 may be provided at the gantry 100. Also, the display 114 may be a desktop type, or implemented as a tablet terminal or the like capable of wireless communications with the memory 112, the processing circuitry 116, etc.

An input interface 115 is provided, which is realized by components for enabling setting of a region of interest (ROI) and so on, and such components include a trackball, switch buttons, a mouse, a keyboard, a touch pad which allows an input operation through contacting its operation screen, and a touch panel display which integrates a display screen and a touch pad. The input interface 115 is connected to the processing circuitry 116 and adapted to convert input operations received from an operator, etc., into electric signals and to output the electric signals to the processing circuitry 116. In the disclosure herein, the input interface 115 is not limited to physical operating components such as a mouse and a keyboard. That is, examples of the input interface 115 also include processing circuitry for electric signals, which is adapted to receive an electric signal corresponding to an input operation from an external input device separate from the apparatus, and to output this electric signal to the processing circuitry 116. The input interface 115 may be provided at the gantry 100. The input interface 115 may instead be implemented as a tablet terminal or the like capable of wireless communications with the processing circuitry 116.

The processing circuitry 116 is a processor adapted to realize various functions by invoking one or more programs in the memory 112, and it takes total control over the components and elements in the apparatus. While FIG. 1 assumes that the processing circuitry 116 is a single circuitry element for realizing each of the various functions, the processing circuitry 116 may be constituted by a combination of multiple independent processors each running a program to realize the respective function. Said various functions include, for example, a first setting function 116*a*, a second setting function 116*b*, and an adjustment function 116*c*. Note that the second setting function 116*b* and the adjustment function 116*c* are optional features that may be discretionarily adopted or omitted.

The first setting function 116*a* is a function to set, based on the reference image, imaging conditions used in the scanning for the subject. For example, the first setting function 116*a* sets imaging conditions of a tube current and others based on calculations for auto-exposure control (AEC) so that imaging control can take into account the thickness of the subject or its site for absorbing X-rays. The imaging conditions here include, for example, a tube current, a tube voltage, a DAS sensitivity (ADC full scale, ADC reference voltage, amplification degree of the amplifier system, etc.), and so on. The manner of setting the imaging conditions by the first setting function 116*a* may be automatic or semiautomatic. When the automatic manner is adopted, the first setting function 116*a* automatically sets the calculated imaging conditions. When the semiautomatic manner is adopted, the first setting function 116*a* sets the calculated imaging conditions upon approval from a user or the like. More concretely, and for example, the first setting function 116*a* may cause the display 114 to display the calculated imaging conditions to prompt user's approval, and may set the imaging conditions upon receiving an instruction with the approval on the imaging conditions via the input interface 115. In any case, the set imaging conditions will be used by the scan controller 110 for controlling the scanning.

The second setting function 116*b* is a function to set an imaging range for the subject using an area projector 118 in advance of the scanning. In an exemplary implementation with this function, a projector controller 117 controls the area projector 118 according to an imaging range input via the input interface 115 so that the area projector 118 scans with a light beam to project a frame sign indicative of the imaging range onto the subject. The second setting function 116*b* sets the current imaging range upon receiving an instruction to fix the imaging range via the input interface 115.

The adjustment function 116*c* is a function to adjust, with the use of the reference image, the imaging range used in the scanning. For example, the adjustment function 116*c* adjusts the imaging range in response to an input of information, such as an upper limit or a lower limit of the imaging range, via the input interface 115 while the reference image is displayed. The adjusted imaging range is used by the first setting function 116*a* for the AEC calculations.

Additionally, the processing circuitry 116 may also be adapted so that, in response to the input interface 115 being operated based on the reference image and reconstruction conditions (reconstruction position, reconstruction range, slice thickness, reconstruction functions, etc.) being thereby set, it generates scan plan information according to the set reconstruction conditions, imaging conditions, imaging range, etc. The reconstruction conditions may be set immediately before the scanning, or immediately before reconstruction processing after the scanning. The scan plan information is sent to the scan controller 110 so that the scanning may be performed under the control of the scan controller 110 according to the scan plan information.

The projector controller 117 controls the light-beam scan of the area projector 118 according to an imaging range input via the input interface 115.

The area projector 118 includes, for example, multiple light sources which may be light-emitting diodes, laser diodes, etc., and a scanning unit to scan with the light beam emitted from each light source. The area projector 118 is adapted to perform light-beam scan so that a frame sign is projected onto the subject, under the control of the projector controller 117.

Note that the preprocessing circuitry 106, the scan controller 110, the memory 112, the image processing circuitry 113, the display 114, the input interface 115, and the processing circuitry 116 may be furnished on a non-illustrated console unit. Such a console unit is assumed to be an apparatus separate from the gantry 100, but the embodiment tolerates the console unit being incorporated into the gantry 100 or its components being partially included in the gantry 100. Also, the console unit is not limited to a configuration of a single console performing multiple functions, and the console unit may be constituted by different consoles performing the multiple functions. For example, functions of the preprocessing circuitry 106 and the processing circuitry 116 may be distributed.

Next, operations of the X-ray CT apparatus configured as above will be described with reference to the flowcharts in FIG. 2. The description will first refer to FIG. 2(*a*) for the operations of the X-ray CT apparatus according to the embodiment. The description will then refer to FIG. 2(*b*) for the operations according to a comparative example. Hereinafter, the rotation of the X-ray tube unit 101 and the X-ray detector 103, as well as the rotation of the rotary frame 102, may be simply called "gantry rotation".

[Step ST10]: By this step, as shown in FIG. 2(*a*), the X-ray CT apparatus is set with the position of a subject (patient) and the imaging range for the subject.

More specifically, and for example, the subject placed on the couch top of the couch unit 111 is interposed between the X-ray tube unit 101 and the X-ray detector 103. The couch top is moved forward and backward along its longitudinal direction by the non-illustrated driver. The subject (patient) is thus set at the imaging point, and also the imaging range for the subject is set. Note that the imaging range for the subject may be set by using the area projector 118 in advance of obtaining the reference image.

After the position of the subject is set, the couch top of the couch unit 111 is stopped until completion of the scanning.

[Step ST20]: In the X-ray CT apparatus, projection data for generating the reference image is acquired under the control of the scan controller 110, by initiating the gantry rotation with the couch top kept stationary, and switching on and off the radiation of X-rays from the predetermined position around the rotational axis during rotation of the rotary frame 102 in such a manner to realize a reduced X-ray irradiation time. In acquiring the projection data, conventionally known techniques such as the use of pulsed X-ray emissions may be adopted, and how to acquire the projection data is not limited. For example, switching on and off the radiation of X-rays for reducing the X-ray irradiation time is achieved by using pulse signals to control the application of a tube voltage between the anode and cathode of the X-ray tube. Also for example, the amount of thermal electrons flying from the cathode to the anode can be controlled by the application of a grid voltage with respect to the cathode potential, and this property may be utilized to achieve switching on and off the radiation of X-rays for reducing the X-ray irradiation time.

For concrete implementation, as one example, the X-ray tube unit 101 and the X-ray detector 103 are rotated about the rotational axis. However, if the X-ray tube unit 101 and the X-ray detector 103 are located at their respective predetermined positions for the subject, they may remain at the same positions without being rotated. X-rays are radiated from the X-ray tube unit 101 at the predetermined position for just a period required to perform the on/off control of the radiation. Here, the period required to perform the on/off control of the radiation may be interpreted as, if the on/off control of the radiation of X-rays in one-view units is possible, the time required to acquire data for one view. If the on/off control in one-view units is not possible, the time required to acquire a set of data for multiple views (e.g., 2 views, 3 views, etc.) may be adopted. In the latter case, generating a scanogram by summing up the data set for the multiple views can provide an enhanced image quality as compared to the scanogram based on the single view. As such, when generating a scanogram by summing up the data set for multiple views, X-ray irradiation can be performed while the exposure dose is reduced by lowering the tube current value as long as the generated scanogram qualifies as the reference image, and therefore, the patient can receive the benefit of being subjected to a further reduced exposure. Also, said period may correspond to the shortest-possible data acquisition time that is required to obtain one scanogram. In any case, the period required to perform the on/off control of the radiation is significantly shorter than a period required for the rotary frame 102 to complete one rotation. Note that the period of radiation of X-rays is not limited to the period required to perform the on/off control of the radiation, but the X-rays may instead be radiated for just a period that would allow for obtaining one fluoroscopic image or just a period corresponding to one or more views.

In the X-ray CT apparatus performing this step, thus, the scan controller 110 performs control so that cone beam-shaped X-rays are radiated from the X-ray tube unit 101 at the predetermined position on the rotary frame 102 around the rotational axis for the period required to acquire data for at least one view. These X-rays pass through the subject and are detected by the X-ray detector 103. The data acquisition circuitry 104, based on the output from the X-ray detector at that time, sends the corresponding pure raw data to the preprocessing circuitry 106 via the non-contact type data transmitter 105. The preprocessing circuitry 106 subjects the pure raw data to processing such as sensitivity correction, logarithmic conversion, etc., to generate projection data. The projection data is then collected (stored) in the memory 112.

Subsequently, the image processing circuitry 113 generates the reference image of the subject based on the projection data in the memory 112. In the instance where multiple reference images are taken in two respective directions, step ST20 is performed in the same manner for each of the two predetermined positions around the rotational axis. The scan controller 110 also controls the gantry 100 so that the radiation of X-rays is suspended and the rotation of the rotary frame 102 is continued for the period after completion of the X-ray irradiation for generating the reference image and until start of the scanning. When the reference images are taken in two directions, this control is performed for the period after completion of the X-ray irradiations in the two directions and until start of the scanning.

[Step ST30]: In the X-ray CT apparatus, imaging conditions for a tomogram of the subject are set by AEC calculations based on the reference image.

More specifically, and for example, the processing circuitry 116 with the first setting function 116a sets the imaging conditions of a tube current, etc. based on the AEC calculations so that imaging control can take into account the thickness of the subject or its site for absorbing the X-rays. One or more values from, for example, the tube current, the tube voltage, the DAS sensitivity (ADC full scale, ADC reference voltage, amplification degree of the amplifier system, etc.), and so on are adjusted and set as the imaging conditions.

Note that this step ST30 lets the rotation of the X-ray tube unit 101 and the X-ray detector 103, which was initiated in step ST20, continue.

[Step ST40]: In the X-ray CT apparatus, the scanning is performed according to the set imaging conditions. At this time, the processing circuitry 116 controls the scanning based on the set imaging conditions.

The scanning according to the embodiment is then finished.

Next, the operations of an X-ray CT apparatus according to the conventional configuration will be described as a comparative example, with reference to FIG. 2(b).

[Step ST10_pri]: In the state that the rotation of an X-ray tube unit and an X-ray detector is halted, the position of a subject (patient) and the starting point for scanogram imaging are set. More specifically, and for example, the subject placed on the couch top of a couch unit is interposed between the X-ray tube unit and the X-ray detector. The couch top is moved forward and backward along its longitudinal direction by a non-illustrated driver. Thereby, the position of the subject (patient) and the starting point for scanogram imaging are set. The couch top of the couch unit is stationary then.

[Step ST20_pri]: The X-ray CT apparatus initiates the movement of the couch top to start the scanogram imaging, and acquires projection data for generating a scanogram. More specifically, and for example, the X-ray tube unit and the X-ray detector are arranged at their respective predetermined positions for the subject, and the scanogram is taken while the couch top is moved with the X-ray tube unit caused to radiate fan-shaped X-rays.

[Step ST30A_pri]: In the X-ray CT apparatus, imaging conditions for scanning are set by AEC calculations based on the scanogram obtained.

[Step ST30B_pri]: In parallel with step ST30A_pri, the couch top of the couch unit is moved to the starting point for the scanning, and the rotation of the X-ray tube unit and the X-ray detector is initiated to wait for establishment of the gantry rotation.

[Step ST40_pri]: In the X-ray CT apparatus, the scanning is performed according to the set imaging conditions. More specifically, and for example, the scanning is performed while the X-ray tube unit and the X-ray detector are rotated about the body axis, and while the X-ray tube unit is caused to radiate fan-shaped X-rays.

The scanning according to the conventional configuration is then finished.

According to the present embodiment as described above, cone beam-shaped X-rays are radiated and detected after having passed through a subject, and the reference image of the subject is generated based on the output from the area detector (X-ray detector 103) that is given in response to the radiation of the X-rays from the predetermined position around the rotational axis for a period required to perform the on/off control of the radiation. Imaging conditions for use in the scanning for the subject are set based on the generated reference image. The subsequent scanning is controlled based on the set imaging conditions. Note that, when obtaining the reference image, the X-ray source (X-ray tube unit) and the area detector may be either in the state of ongoing rotation or in the stationary state. Also, the X-rays for generating the reference image may be radiated for, instead of the period required to perform the on/off control of the radiation, a period that allows for obtaining one fluoroscopic image or a period corresponding to one or more views.

In sum, the embodiment employs the X-ray tube for radiating cone beam-shaped X-rays and the area detector for detecting the X-rays, and is capable of obtaining the reference image by causing the X-ray tube to radiate the X-rays at the predetermined position for a short period. When taking the reference image, the couch is not driven to move, and the tube position of the X-ray tube is changed according to the rotation of the rotary frame, and therefore, the embodiment can reduce the operation time in even the instances of independently obtaining multiple reference images in multiple directions. Moreover, since the movement of the couch is not required also after the reference image is obtained, the embodiment can reduce the setup time up to the scanning.

In addition to the above, the embodiment eliminates at least the necessity of performing the operation of moving the couch among the operations in steps ST20 to ST30 including the couch movement and the gantry rotation establishment, and as such, the embodiment can complete the acquisition of the reference image data and the subsequent processing in a matter of several seconds. Also, the embodiment achieves a higher efficiency of using X-rays (in the slice thickness direction) than the conventional scanogram imaging, so the reduction of exposure dose can be expected. Moreover, if timing adjustment is needed in relation to the use of a contrast medium, etc., such as the case where the imaging should be performed after 90 seconds from injection of a contrast medium, the embodiment tolerates interposition of a wait time or other processing before the AEC calculations or the scanning. Note that the reference image may be taken before or after injection of a contrast medium.

In contrast, according to the conventional configuration, a subject is set at the starting point for scanogram imaging, and the scanogram imaging is performed while the couch is moved. Then, the couch is returned to the original position as the imaging starting point, and upon establishing the gantry rotation and executing the AEC calculations, the scanning is performed. As such, the conventional configuration requires the couch movement and the gantry rotation establishment between the scanogram imaging in step ST20_pri and the scanning in step ST40_pri, and therefore, it must consume an operation time of 10-second units. More specifically, the conventional scanogram imaging needs to drive and move the couch, and due to this, it takes time depending on the distance traveled by the couch. Also, when scanograms are independently obtained in two directions, e.g., the front direction and the side direction, the conventional scanogram imaging needs to take time to change the tube position of the X-ray tube. Furthermore, after the scanogram imaging, the conventional configuration must use a long setup time involving the couch movement and the gantry rotation establishment before start of the scanning.

According to the embodiment, it is possible to suspend the radiation of X-rays and continue the rotation of the rotary frame for the period after completion of the X-ray irradiation for generating the reference image and until start of the scanning, and therefore, the embodiment can suppress an unnecessary exposure and also allows the gantry rotation to be maintained while waiting for the start of the scanning.

Second Embodiment

Figure 3:
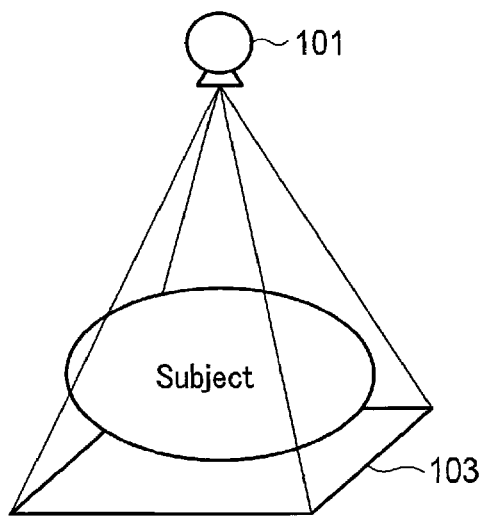
FIG. 3 is a schematic diagram for explaining projection data acquired by an X-ray CT apparatus according to a second embodiment.

Next, an X-ray CT apparatus according to the second embodiment will be described with reference to FIG. 3.

The second embodiment may be understood as a modification of the first embodiment, and it particularly relates to the generation of the reference image in step ST20. Specifically, with the configuration as shown in FIG. 3, where cone beam-shaped X-rays are radiated from the X-ray tube unit 101, pass through a subject, and are detected by the X-ray detector 103, the reference image is basically generated from projection data for one view within one rotation of the rotary frame. That is, the acquisition of projection data for generating the reference image is normally complete upon one rotation of the rotary frame. For generating the reference image, the projection data for one view is basically used, but depending on the cases, a set of projection data for multiple views may be used. When projection data set for multiple views is used, X-ray irradiation doses corresponding to the respective views can be suppressed by, for example, performing control such as lowering the tube current of the X-ray tube at the time of halting the rotation of the gantry and radiating the X-rays. Also for example, the projection data set for multiple views, acquired from the gantry rotation, may be superimposed together to generate the reference image. Accordingly, the generation of the reference image may adopt any of the following manners (a) to (a).

(a) With or without the gantry rotation, the reference image may be generated from the projection data for one view given based on the radiation of X-rays from the predetermined position around the rotational axis for as long period as required to perform the on/off control of the radiation. The projection data here is used as the reference image data. The manner (a) conforms to the first embodiment.

(b) When obtaining the reference image with the gantry rotation halted, the reference image may be generated by superimposing the projection data set for multiple views given based on the radiation of X-rays from the predetermined position around the rotational axis for as long period as required to perform the on/off control of the radiation. The multiple views in the manner (b) here may be discretionarily set in the range of, for example, from 2 to 10 views. According to the manner (b), even when time is required to control turning on and off of the radiation of X-rays, the imaging operation can be performed with a lowered tube current, etc., and therefore, at the level of suppressed X-ray irradiation doses from the X-ray tube unit 101 that remains at the predetermined position.

(c) When obtaining the reference image while the gantry rotation is ongoing, the reference image may be generated by, as long as the influence of a blur is kept ignorable, superimposing the projection data set for multiple views given based on the radiation of X-rays from the predetermined position around the rotational axis for as long period as required to perform the on/off-control of the radiation. The multiple views in this manner (c) may be, for example, multiple views that form an on/off controllable unit when the on/off control of X-rays is not very smooth and it is difficult to perform the on/off control of X-ray irradiation in one-view units.

In any of the manners (a) to (c), the X-ray irradiation time is controlled so that it does not largely exceed the data acquisition time. This is applicable also to the cases where the radiation of X-rays for obtaining the reference image is performed for a period that would allow for obtaining one fluoroscopic image or a period corresponding to one or more views, instead of the period required to perform the on/off control of the radiation.

Also, in any of the manners (a) to (c), the reference image is generated by the X-ray CT apparatus performing the same operation as in step ST20 described for the foregoing embodiment, according to the information input via the input interface 115 that may include the imaging conditions of a tube current, etc., the desired number of imaging operations, and so on.

Therefore, according to the second embodiment, where the reference image is generated by superimposing the projection data set for multiple views given based on the short-time radiation of X-rays from the predetermined position around the rotational axis, an advantage of suppressing the X-ray irradiation doses can be attained in addition to the effects and advantages as in the first embodiment.

Third Embodiment

Next, an X-ray CT apparatus according to the third embodiment will be described.

The third embodiment may be understood as a concrete example of some aspects of the first embodiment and the second embodiment, and it particularly relates to the predetermined position around the rotational axis as used in step ST20. Specifically, according to this embodiment, the scan controller 110 performs at least one of the second control function and/or the third control function.

The second control function is a function to control the X-ray tube unit 101 to radiate X-rays using, as the predetermined position, either the 0° position at the top of the trajectory around the rotational axis or the 180° position at the bottom of the trajectory, whichever is closer to the position of the X-ray tube unit 101 on the trajectory at the time that an instruction to start taking the reference image is given.

The third control function is a function to control the X-ray tube unit 101 to radiate X-rays using, as the predetermined position, either the 90° position or the 270° position at the respective midpoint between the top and bottom of the trajectory around the rotational axis, whichever is closer to the position of the X-ray tube unit 101 on the trajectory at the time that the instruction to start taking the reference image is given.

How the scan controller 110 operates in step ST20 will be described with reference to the schematic diagrams given in FIGS. 4 to 7. The description will assume exemplary instances where the subject lies on its back for explanation of the operations including obtaining the reference image with the gantry kept rotated. The explanation will be given in the order of case (a) where the 0° position or the 180° position is used, case (b) where the 90° position or the 270° position is used, case (c) where any of the positions from the cases (a) and (b) may be used, and case (d) where imaging is performed in two directions.

Figure 4:
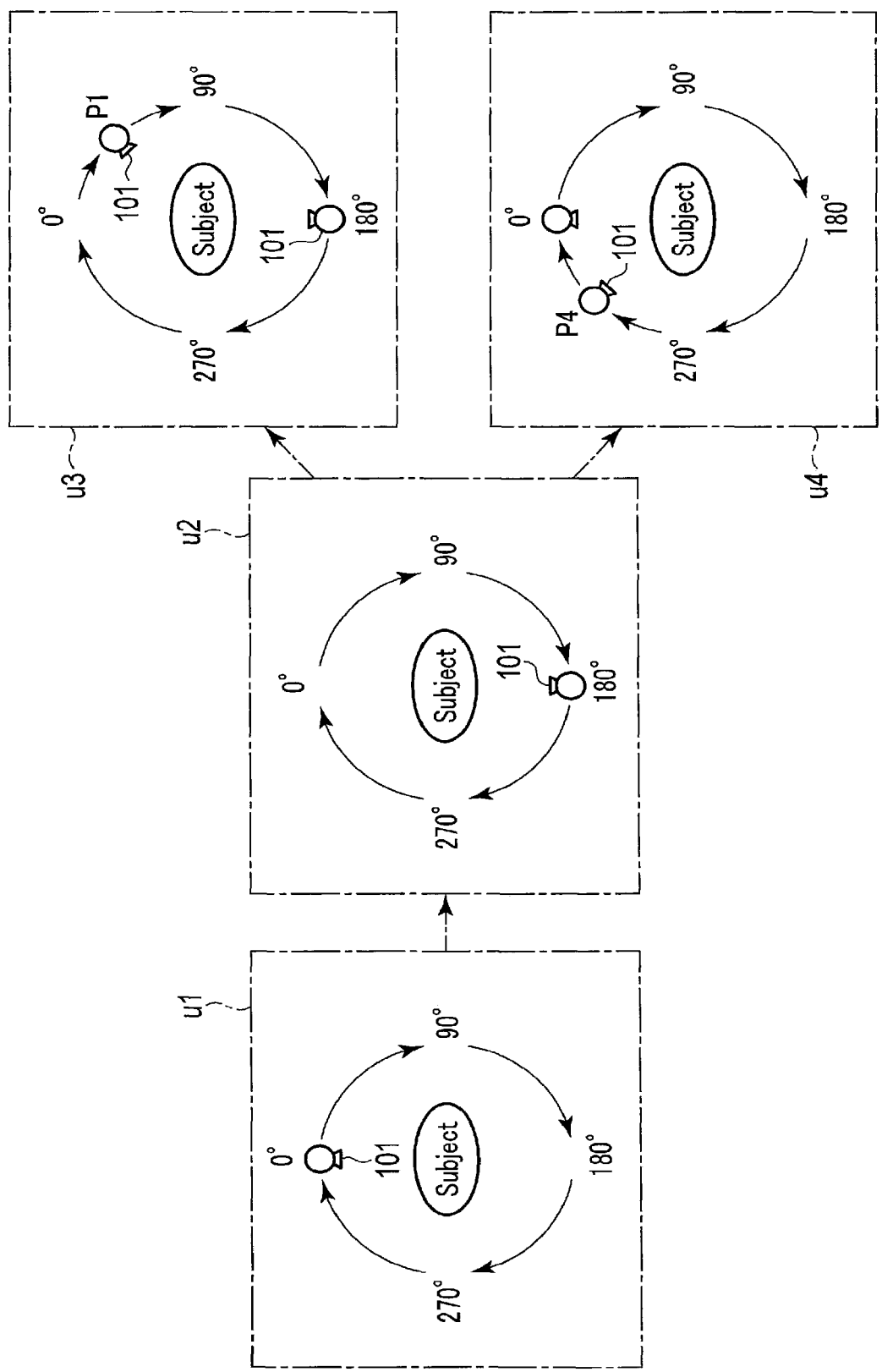
FIG. 4 includes schematic diagrams for explaining a certain operation of an X-ray CT apparatus according to a third embodiment.

(a) Case where the 0° position or the 180° position is used (case of the anteroposterior direction):

The reference image taken in the anteroposterior direction for use in the AEC calculations is typically a top image. In this case, the reference image may be obtained by the X-ray irradiation using, as the predetermined position, the 0° position at the top of the trajectory around the rotational axis, as shown in FIG. 4, state u1.

When the reference image taken in the anteroposterior direction is to be used, such a reference image is not limited to the top image, and a bottom image may instead be obtained as the reference image by using, as the predetermined position, the 180° position at the bottom of the trajectory around the rotational axis, as shown in the figure, state u2.

That is, in response to designation of the reference image in the anteroposterior direction, the reference image may be taken using the 0° position or the 180° position as the predetermined position.

In actual implementation, as shown in state u3 as one example, the scan controller 110 controls the X-ray tube unit 101 to radiate X-rays using, as the predetermined position, one of the 0° position and the 180° position that is closer to the position P1 of the X-ray tube unit 101 around the rotational axis at the time that an instruction to start taking the reference image is given (namely, in this example, the 180° position).

Alternatively, as shown in state u4 as another example, the scan controller 110 controls the X-ray tube unit 101 to radiate X-rays using, as the predetermined position, one of the 0° position and the 180° position that is closer to the position P4 of the X-ray tube unit 101 around the rotational axis at the time that an instruction to start taking the reference image is given (namely, in this example, the 0° position).

In either case, the position closer to the X-ray tube unit 101 at the receipt of the instruction to start imaging is adopted as the predetermined position, and the radiation of X-rays is performed at this predetermined position, whereby the reference image can be obtained more quickly.

Figure 5:
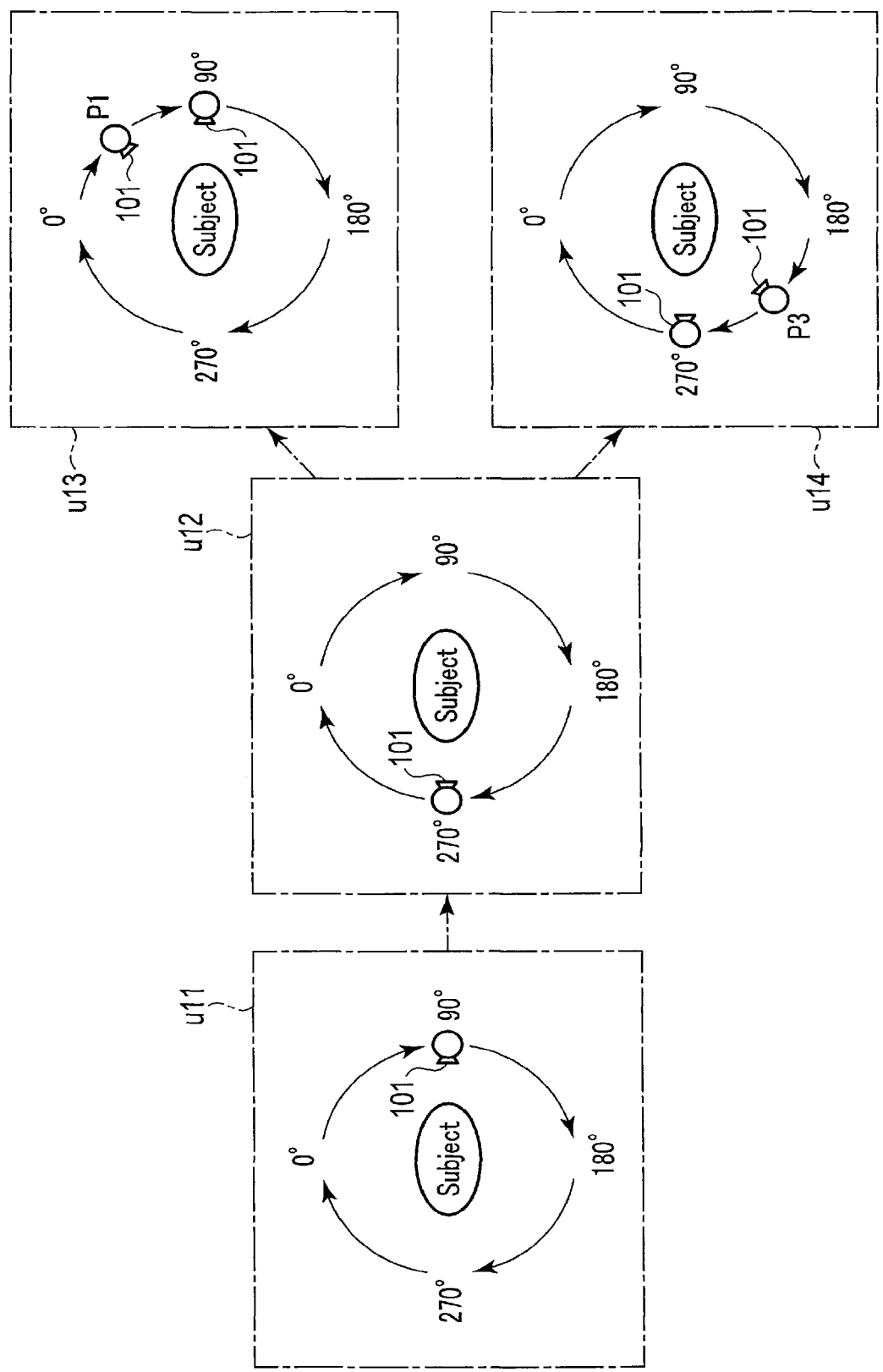
FIG. 5 includes schematic diagrams explaining a modification of the certain operation according to the embodiment.

(b) Case where the 90° position or the 270° position is used (case of the lateral direction):

When the reference image taken in the lateral direction is to be used in the AEC calculations, the reference image may be obtained by the X-ray irradiation using, as the predetermined position, the 90° position at the midpoint between the top and bottom of the trajectory around the rotational axis, as shown in FIG. 5, state u11. Note that the reference image in the lateral direction may be obtained instead by using, as the predetermined position, the 270° position at the other midpoint between the top and bottom of the trajectory around the rotational axis, as shown in the figure, state u12.

That is, in response to designation of the reference image in the lateral direction, the reference image may be taken using the 90° position or the 270° position as the predetermined position.

In actual implementation, as shown in state u13 as one example, the scan controller 110 controls the X-ray tube unit 101 to radiate X-rays using, as the predetermined position, one of the 90° position and the 270° position that is closer to the position P1 of the X-ray tube unit 101 around the rotational axis at the time that an instruction to start taking the reference image is given (namely, in this example, the 90° position).

Alternatively, as shown in state u14 as another example, the scan controller 110 controls the X-ray tube unit 101 to radiate X-rays using, as the predetermined position, one of the 90° position and the 270° position that is closer to the position P3 of the X-ray tube unit 101 around the rotational axis at the time that an instruction to start taking the reference image is given (namely, in this example, the 270° position).

In either case, the position closer to the X-ray tube unit 101 at the receipt of the instruction to start imaging is adopted as the predetermined position, and the radiation of X-rays is performed at this predetermined position, whereby the reference image can be obtained more quickly.

(c) Case where any of the positions from the cases (a) and (b) may be used (case of the anteroposterior or lateral direction):

When the reference image taken in the anteroposterior or lateral direction is to be used in the AEC calculations, the reference image may be obtained by the X-ray irradiation using, as the predetermined position, one of the angle positions at 0°, 90°, 180°, and 270° that is closest to the X-ray tube unit 101 in the rotating state, as shown in FIG. 6, state u21.

That is, as shown in state u22 as one example, the scan controller 110 controls the X-ray tube unit 101 to radiate. X-rays using, as the predetermined position, one of the 0° position, the 90° position, the 180° position, and the 270° position around the rotational axis that is closest to the position P2 of the X-ray tube unit 101 around the rotational axis at the time that an instruction to start taking the reference image is given (namely, in this example, the 180° position).

As a different occasion, as shown in state u23 as another example, the scan controller 110 controls the X-ray tube unit 101 to radiate. X-rays using, as the predetermined position, one of the 0° position, the 90° position, the 180° position, and the 270° position around the rotational axis that is closest to the position P3 of the X-ray tube unit 101 around the rotational axis at the time that an instruction to start taking the reference image is given (namely, in this example, the 270° position).

In any case, the position closest to the X-ray tube unit 101 at the receipt of the instruction to start imaging is adopted as the predetermined position, and the radiation of X-rays is performed at this predetermined position, whereby the reference image can be obtained more quickly.

Figure 7:
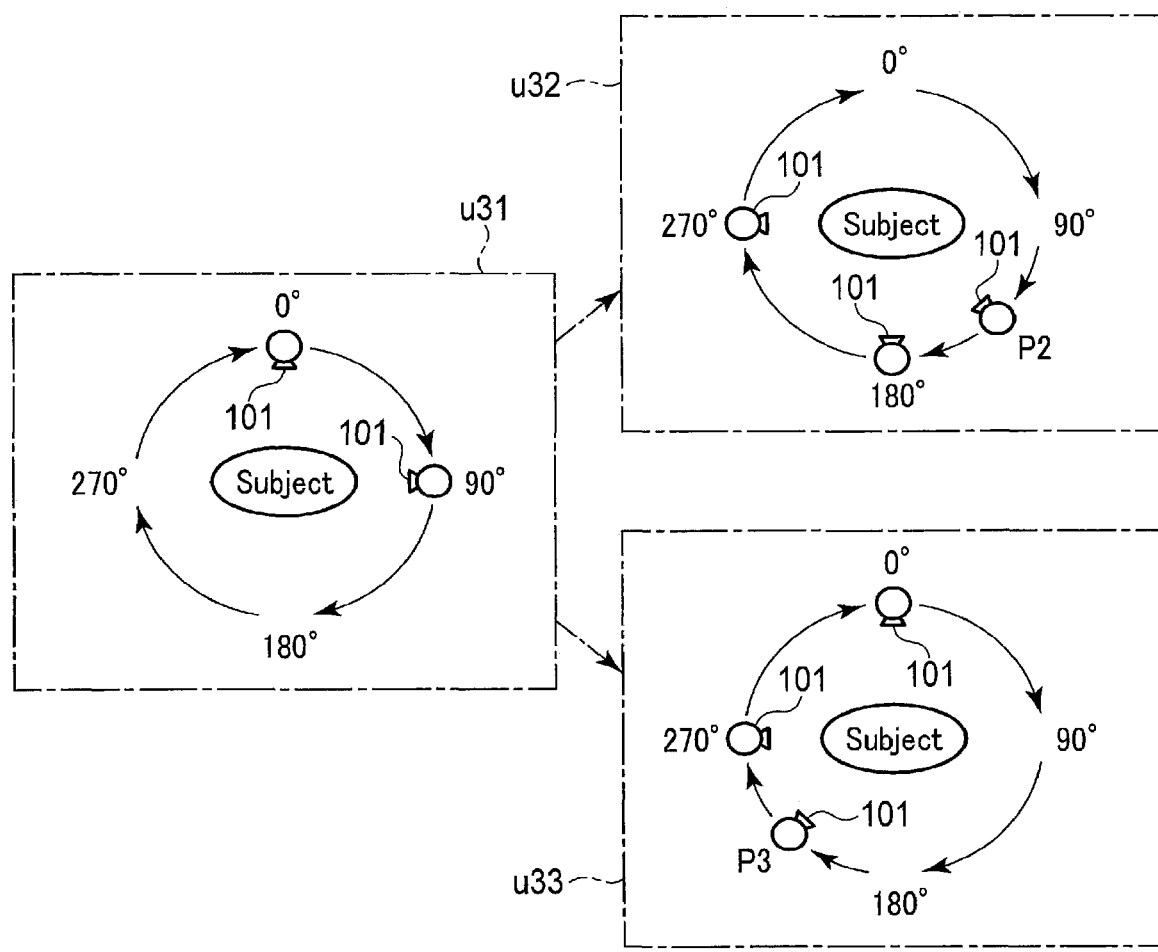
FIG. 7 includes schematic diagrams for explaining yet another modification of the certain operation according to the embodiment.

(d) Case where imaging is performed in two directions (case of both the anteroposterior and lateral directions):

When the reference images taken in the respective anteroposterior and lateral directions are to be used in the AEC calculations, the reference images may be obtained by the X-ray irradiation using, as the predetermined positions, two consecutive angle positions among the 0° position, the 90° position, the 180° position, and the 270° position as shown in FIG. 7, state u31.

That is, as shown in state u32 as one example, the scan controller 110 controls the X-ray tube unit 101 to sequentially radiate X-rays using, as the respective predetermined positions, two consecutive angle positions that are closest to the position P2 of the X-ray tube unit 101 at the time that an instruction to start taking the reference images is given (namely, in this example, the 180° position and the 270° position).

As a different occasion, as shown in state u33 as another example, the scan controller 110 controls the X-ray tube unit 101 to sequentially radiate X-rays using, as the respective predetermined positions, two consecutive angle positions that are closest to the position P3 of the X-ray tube unit 101 at the time that an instruction to start taking the reference images is given (namely, in this example, the 270° position and the 0° position).

In any case, the positions closest to the X-ray tube unit 101 at the receipt of the instruction to start imaging is adopted as the predetermined positions, and the radiation of X-rays is performed sequentially at these predetermined positions, whereby the reference images can be obtained more quickly. Note that, if the apparatus adopts a dual-tube type configuration where two X-ray tubes are arranged at an angle of approximately 90', the reference images may be obtained at once by simultaneously using the closest two consecutive angle positions.

According to the present embodiment as described above, the X-ray tube unit 101 may be controlled to radiate X-rays using, as the predetermined position, either the 0° position at the top of the trajectory around the rotational axis or the 180° position at the bottom of the trajectory, whichever is closer to the position of the X-ray tube unit 101 around the rotational axis at the time that an instruction to start taking the reference image is given. Also, the X-ray tube unit 101 may be controlled to radiate X-rays using, as the predetermined position, either the 90° position or the 270° position at the respective midpoint between the top and bottom of the trajectory around the rotational axis, whichever is closer to the position of the X-ray tube unit 101 around the rotational axis at the time that the instruction to start taking the reference image is given.

Therefore, according to the third embodiment, where the position closer to the X-ray tube unit 101 at the receipt of the instruction to start imaging is adopted as the predetermined position and the radiation of X-rays is performed at this predetermined position while the X-ray tube unit 101 is rotated about the rotational axis, an advantage of more quickly obtaining the reference image can be attained in addition to the effects and advantages as in the first and second embodiments.

Fourth Embodiment

Next, an X-ray CT apparatus according to the fourth embodiment will be described.

Figure 8A:
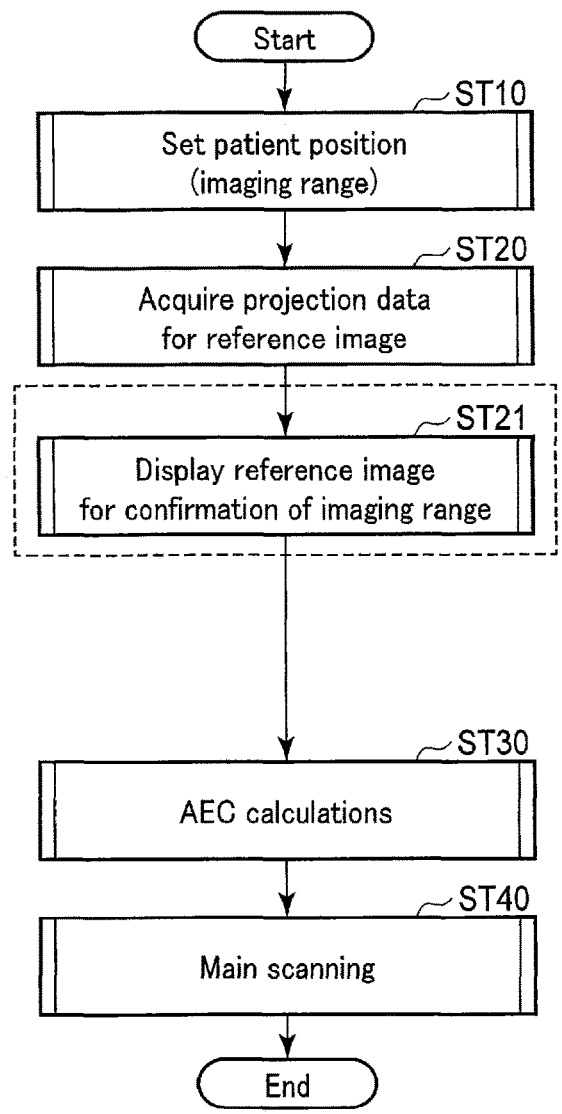
FIG. 8A is a flowchart for explaining an operational sequence of an X-ray CT apparatus according to a fourth embodiment.
Figure 8B:
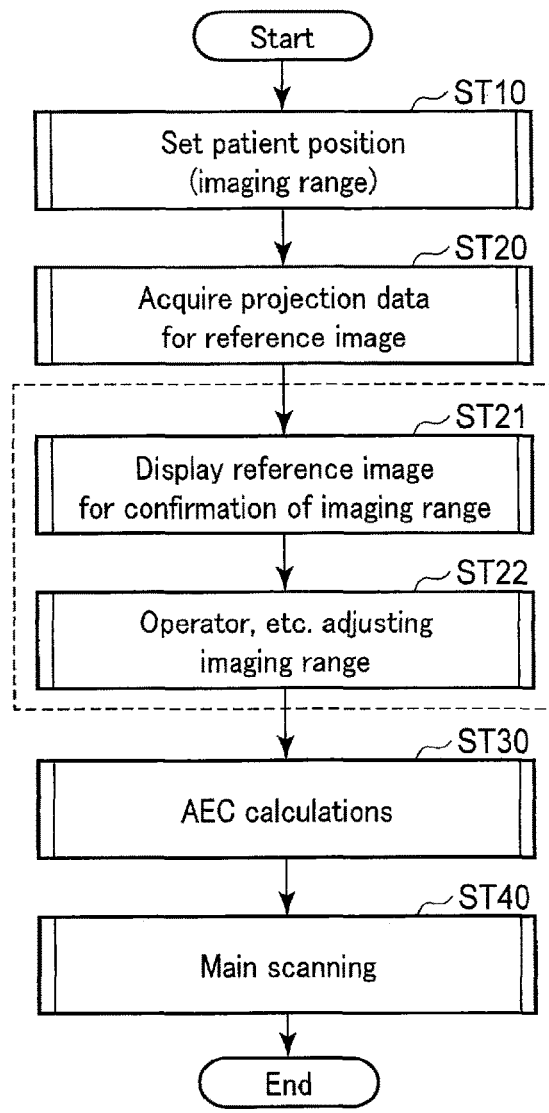
FIG. 8B is a flowchart for explaining a modification of the operational sequence shown in FIG. 8A.

The fourth embodiment may be understood as a modification of the first to third embodiments, and it involves displaying the reference image for confirmation, adjustment, etc. of the imaging range as emphasized by dashed boxes in FIGS. 8A and 8B. More specifically, this embodiment relates to the configuration where the processing circuitry 116 performs the second setting function 116*b* and the adjustment function 116*c* as appropriate.

Figure 9A:
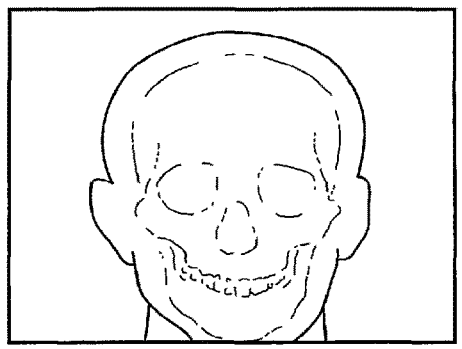
FIG. 9A is a schematic diagram for explaining the operations shown in FIG. 8A.

In the example shown in FIG. 8A, the X-ray CT apparatus displays, after completion of step ST20, the reference image data having been obtained using the predetermined position so that the imaging range can be confirmed (step ST21). The user, etc. are thus allowed to check and confirm the imaging range for the subsequent scanning through the reference image displayed on the display 114 which may be, for example, as shown in FIG. 9A. After the imaging range is confirmed, steps ST30 to ST40 are performed in the manner as described.

Figure 9B:
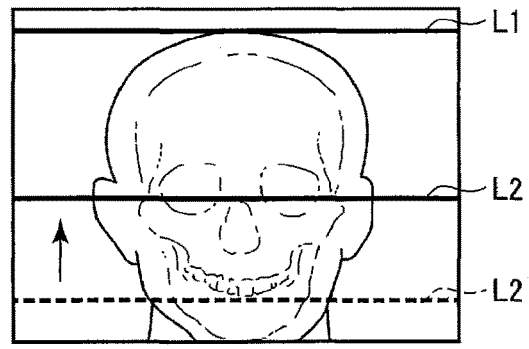
FIG. 9B is a schematic diagram for explaining the modification shown in FIG. 8B.

Also, the imaging range may be adjusted (step ST22) after step ST21, as shown in FIG. 8B. In such an operation, as shown in FIG. 9B for example, the processing circuitry 116 with the adjustment function 116*c* adjusts the imaging range according to information such as an upper limit L1 or a lower limit L2 of the imaging range, input via the input interface 115 while the reference image is displayed together with the indications of the present upper limit L1 and lower limit L2 of the imaging range, and the processing circuitry 116 causes the image processing circuitry 113 to correspondingly move the indication of the lower limit L2 on the display in conjunction with performing this adjustment. In this example, the lower limit L2 of the imaging range is adjusted so that the eye balls of the subject are excluded from the imaging range. The adjusted imaging range is used by the first setting function 116a for the AEC calculations.

Or, the processing circuitry 116 with the second setting function 116b may set an imaging range for the subject using the area projector 118 in advance of the scanning. For example, the projector controller 117 controls the area projector 118 according to an imaging range input via the input interface 115 so that the area projector 118 scans with a light beam to project a frame sign indicative of the imaging range onto the subject. Here, the imaging range marked using the area projector 118 may be adjusted as appropriate in light of a check of the reference image by the operator, etc. (step ST22). The second setting function 116b then sets the current imaging range upon receiving an instruction to fix the imaging range via the input interface 115.

In any case, upon setting the imaging range after the adjustment, the AEC calculations in step ST30 and the scanning in step ST40 are performed in accordance with the set imaging range.

According to the present fourth embodiment as described above, where the imaging range for the scanning is adjusted through the reference image, an advantage of, for example, avoiding exposures of areas susceptible to X-rays (e.g., eye balls) according to the result of checking the reference image by the operator, etc. can be attained in addition to the effects and advantages as in the first to third embodiments.

Further, when the imaging range for the subject is set using the area projector 118 in advance of the scanning, the imaging range marked using the area projector 118 can be adjusted in comparison with the reference image displayed on the display 114.

Fifth Embodiment

Next, an X-ray CT apparatus according to the fifth embodiment will be described.

Figure 10A:
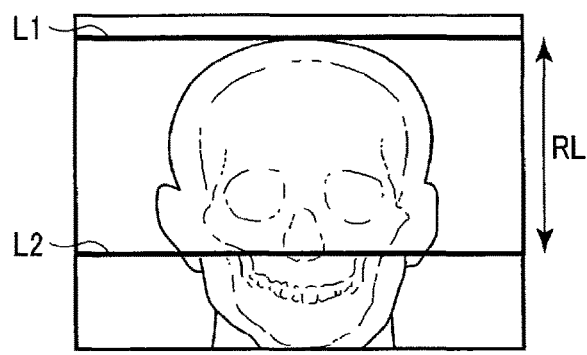
FIG. 10A is a schematic diagram for explaining a certain operation of an X-ray CT apparatus according to a fifth embodiment.
Figure 10B:
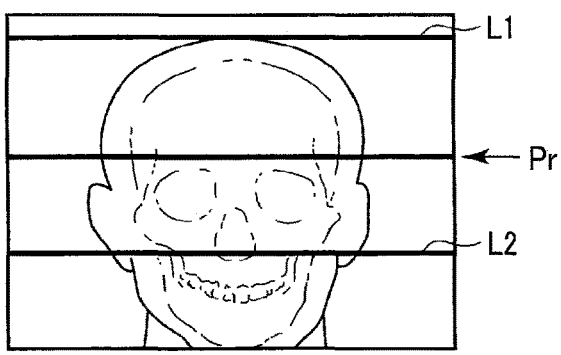
FIG. 10B is a schematic diagram for explaining another operation according to the embodiment.

The fifth embodiment may be understood as a modification of the first to fourth embodiments, and it involves setting a reconstruction range RL and a reconstruction priority position Pr on the displayed reference image as shown in FIGS. 10A and 10B.

Accordingly, the image processing circuitry 113 includes, in addition to the configuration described above, a function of superimposing an upper limit L1 and a lower limit L2 of the reconstruction range RL, input via the input interface 115, onto the reference image being displayed, and a function of performing reconstruction based on the set reconstruction range RL.

Furthermore, the image processing circuitry 113 additionally includes a function of superimposing the reconstruction priority position Pr, input via the input interface 115, onto the reference image being displayed, and a function of performing reconstruction based on the set reconstruction priority position Pr.

Meanwhile, the processing circuitry 116 includes, in addition to the configuration described above, a function of setting the reconstruction range RL based on an instruction to set this reconstruction range RL, input via the input interface 115, during display of the reference image.

Furthermore, the processing circuitry 116 additionally includes a function of setting the reconstruction priority position Pr based on an instruction to set this reconstruction priority position Pr, input via the input interface 115, during display of the reference image.

Description will be given of how each of the reconstruction range RL and the reconstruction priority position Pr is set within the X-ray CT apparatus configured as above. Note that the timing to set the reconstruction range RL and the reconstruction priority position Pr may discretionarily be before the scanning, or at the time of reconstruction processing after the scanning.

(a) Example of Setting the Reconstruction Range RL:

As shown in FIG. 10A, during display of the reference image, the image processing circuitry 113 adds the upper limit L1 and the lower limit L2 of the reconstruction range RL onto the reference image so that they are displayed in a superimposed state, in response to the input of these upper limit L1 and lower limit L2 via the input interface 115. In this state, upon receipt of an instruction to set the reconstruction range RL via the input interface 115, the processing circuitry 116 sets the reconstruction range RL. In the reconstruction step, accordingly, the image processing circuitry 113 performs reconstruction based on the set reconstruction range RL.

(b) Example of Setting the Reconstruction Priority Position Pr:

The purpose of setting the reconstruction priority position Pr is, for example, enabling the reconstruction, display, etc. to be started with a site that can be predicted to be a bleeding site or the like in advance.

As shown in FIG. 10E, during display of the reference image together with the upper limit L1 and the lower limit L2 of the reconstruction range, the image processing circuitry 113 adds the reconstruction priority position Pr onto the reference image so that they are displayed in a superimposed state, in response to the input of this reconstruction priority position Pr via the input interface 115. In this state, upon receipt of an instruction to set the reconstruction priority position Pr via the input interface 115, the processing circuitry 116 sets the reconstruction priority position Pr. In the reconstruction step, accordingly, the image processing circuitry 113 starts reconstruction within the reconstruction range and from the reconstruction priority position Pr.

According to the present embodiment with the configuration of allowing the reconstruction range RL and the reconstruction priority position Pr to be set on the displayed reference image as described above, reconstruction is performed using only the reconstruction range covering a required or desired site among the imaged range, and as such, reconstruction processing for unnecessary sites can be omitted. Moreover, if there is a reconstruction position desired for immediate check, the embodiment enables the reconstruction of such a position to be done ahead of other positions.

Sixth Embodiment

Next, an X-ray CT apparatus according to the sixth embodiment will be described.

Figure 11:
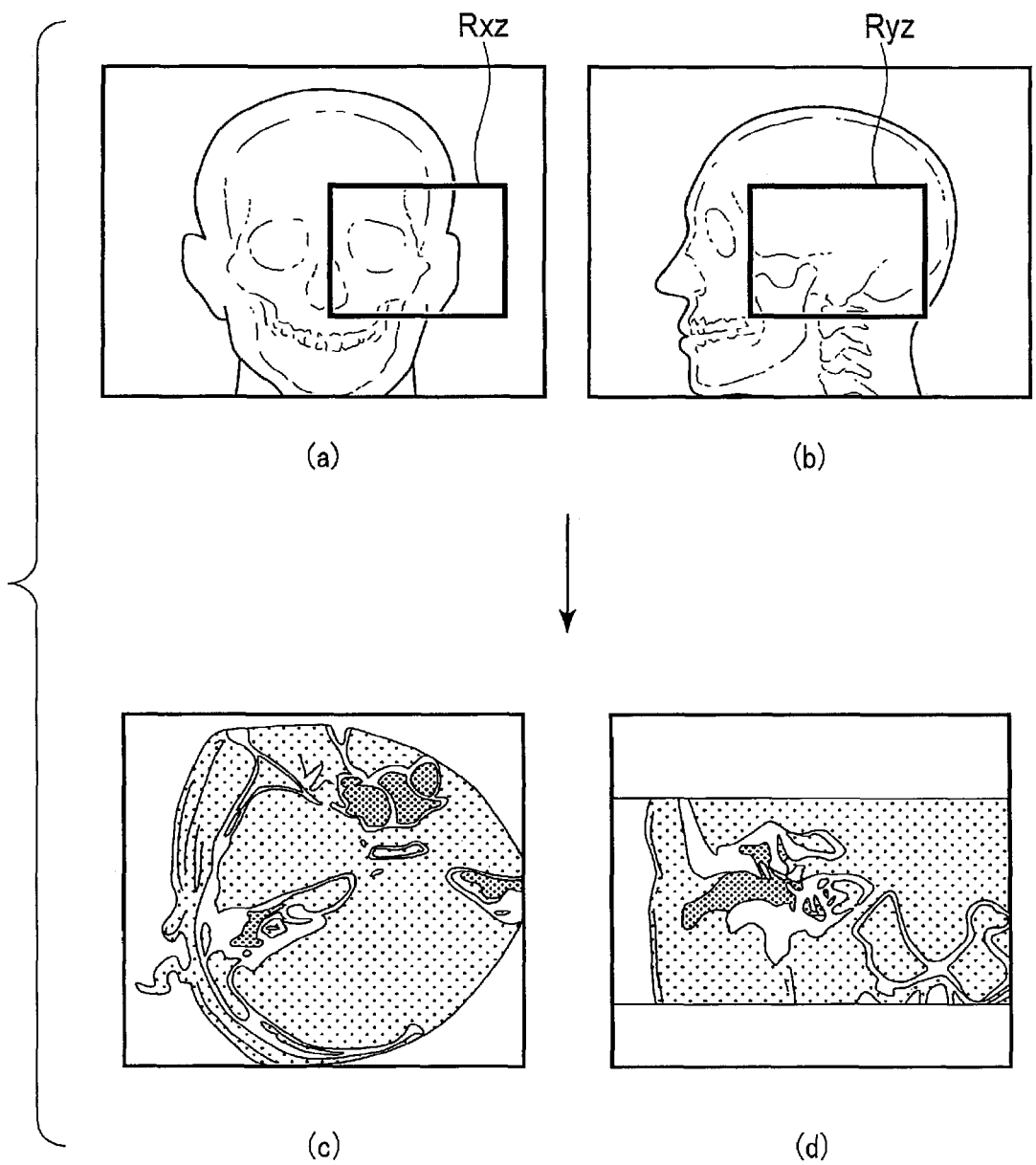
FIG. 11 includes schematic diagrams for explaining a certain operation of an X-ray CT apparatus according to a sixth embodiment.

The sixth embodiment may be understood as a modification of the first to fifth embodiments, and it involves setting a reconstruction range Rxz or Ryz, extending in a common Z-direction and also in one of an X-direction and a Y-direction, on the displayed reference image as shown in the respective schematic diagram in FIG. 11.

Accordingly, the image processing circuitry 113 includes, in addition to the configuration described above, a function of superimposing a Z-direction extension and an X-direction extension for the reconstruction range Rxz, designated via the input interface 115, onto the reference image being displayed, and a function of performing reconstruction based on the set reconstruction range Rxz. The image processing circuitry 113 has similar functions for the reconstruction range Ryz and its Z-direction and Y-direction extensions, as well.

Meanwhile, the processing circuitry 116 includes, in addition to the configuration described above, a function of setting the reconstruction range Rxz based on an instruction to set this reconstruction range Rxz, input via the input interface 115, during display of the reference image. The processing circuitry 116 has similar functions for the reconstruction range Ryz and its Z-direction and Y-direction extensions, as well.

Description will be given of how the reconstruction ranges Rxz and Ryz are set within the X-ray CT apparatus configured as above. Note that the timing to set the reconstruction ranges Rxz and Ryz may discretionarily be before the scanning, or at the time of reconstruction processing after the scanning.

First, when designation of the Z-direction extension and the X-direction extension is received via the input interface 115 during display of the reference image, the processing circuitry 116 sets the reconstruction range Rxz based on these Z-direction and X-direction extensions as shown in, for example, FIG. 11(a). Also, when designation of the Z-direction extension and the Y-direction extension is received via the input interface 115 during display of the reference image, the processing circuitry 116 sets the reconstruction range Ryz based on these Z-direction and Y-direction extensions as shown in, for example, FIG. 11(b). Note that, where multiple reference images are used, the reconstruction ranges Rxz and Rxy in the respective images may be associated with each other such that they are set with the common Z-direction extension, and that the X-direction extension and the Y-direction extension are equalized with each other.

Accordingly, the image processing circuitry 113 performs reconstruction based on the set reconstruction range Rxz and/or reconstruction range Ryz. FIG. 11(c) shows one example of an axial image, and FIG. 11(d) shows one example of a coronal image.

According to the present embodiment with the configuration where the reconstruction ranges Rxz and Ryz, extending in the common Z-direction and also in one of the X-direction and the Y-direction, are allowed to be set on the respective displayed reference images as described above, an advantage of enabling display of tomograms from multiplanar reconstruction (MPR) can be attained in addition to the effects and advantages as in the first to fifth embodiments. Moreover, since reconstruction is performed using only the reconstruction range Rxz and/or the reconstruction range Ryz covering a required or desired site among the imaged range, reconstruction processing for unnecessary sites can be omitted, and a high-speed reconstruction operation can be realized.

Seventh Embodiment

Next, an X-ray CT apparatus according to the seventh embodiment will be described.

The seventh embodiment may be understood as a modification of the first to sixth embodiments, and it involves correcting a distortion in the reference image as will be explained with reference to FIG. 12. Accordingly, the image processing circuitry 113 includes, in addition to the configuration described above, a function of correcting the distortion in such a manner as reprojecting the reference image data that is indicative of a fluoroscopic image distorted due to the curved detection plane of the X-ray detector 103, onto a flat plane so that the distortion is removed.

More specifically, the X-ray detector 103 includes, as shown in FIG. 12, a detection plane 103a having a curved profile in order for the multiple X-ray detecting elements to be located at an equal distance from the focal point (X-ray source F) of the X-ray tube unit 101. Due to this, if the projection data obtained based on the output from the X-ray detector 103 is used as it is, the resultant reference image (fluoroscopic image) of a subject is often displayed with a distortion.

To correct for such a distortion, the image processing circuitry 113 subjects the projection data based on the output from the X-ray detector 103 to the reprojection processing where the projection data is reprojected onto a flat plane $S_o$ orthogonal to an X-ray path $L_o$ that connects the X-ray tube unit 101 to the center of the X-ray detector 103, or onto a flat plane parallel to the plane $S_o$. Note that the plane $S_o$ is also a plane extending through the rotation center O of the gantry 100 and along the X-axis and the X axis. When the plane $S_o$ or a flat plane parallel to the plane $S_o$ is used as a plane onto which the projection data is reprojected, such a plane is called a projection plane.

The image processing circuitry 113 thus subjects the projection data to the reprojection processing to generate the reference image data, and lets the display 114 display the reference image based on this reference image data.

According to the configuration as above, the projection data based on the output from the X-ray detector 103 is subjected to the reprojection processing where the projection data is reprojected onto the flat plane $S_o$ orthogonal to the X-ray path $L_o$ that connects the X-ray tube unit 101 to the center of the X-ray detector 103, or onto a flat plane parallel to the plane $S_o$. The distortion due to the curved detection plane 103a of the X-ray detector 103 is corrected accordingly, and the reference image without the distortion can be used when setting the imaging conditions, etc.

Eighth Embodiment

Next, an X-ray CT apparatus according to the eighth embodiment will be described.

The eighth embodiment may be understood as a modification of the first to seventh embodiments, and it involves performing either the scanogram imaging method according to the foregoing embodiments or the normal scanogram imaging method, depending on an imaging site, examination purpose, etc. Here, the scanogram imaging method according to the foregoing embodiments is intended to be a method of performing the scanogram imaging without the movement of the couch unit 111 as explained with reference to, for example, FIG. 2(a), and this method will be called "first scanogram imaging" below. The normal scanogram imaging method is intended to be a method of performing the scanogram imaging with the movement of the couch unit 111 as explained with reference to, for example, FIG. 2(b), and this method will be called "second scanogram imaging" below. Also, the "examination purpose" may be replaced with "purpose of imaging".

Figure 13:
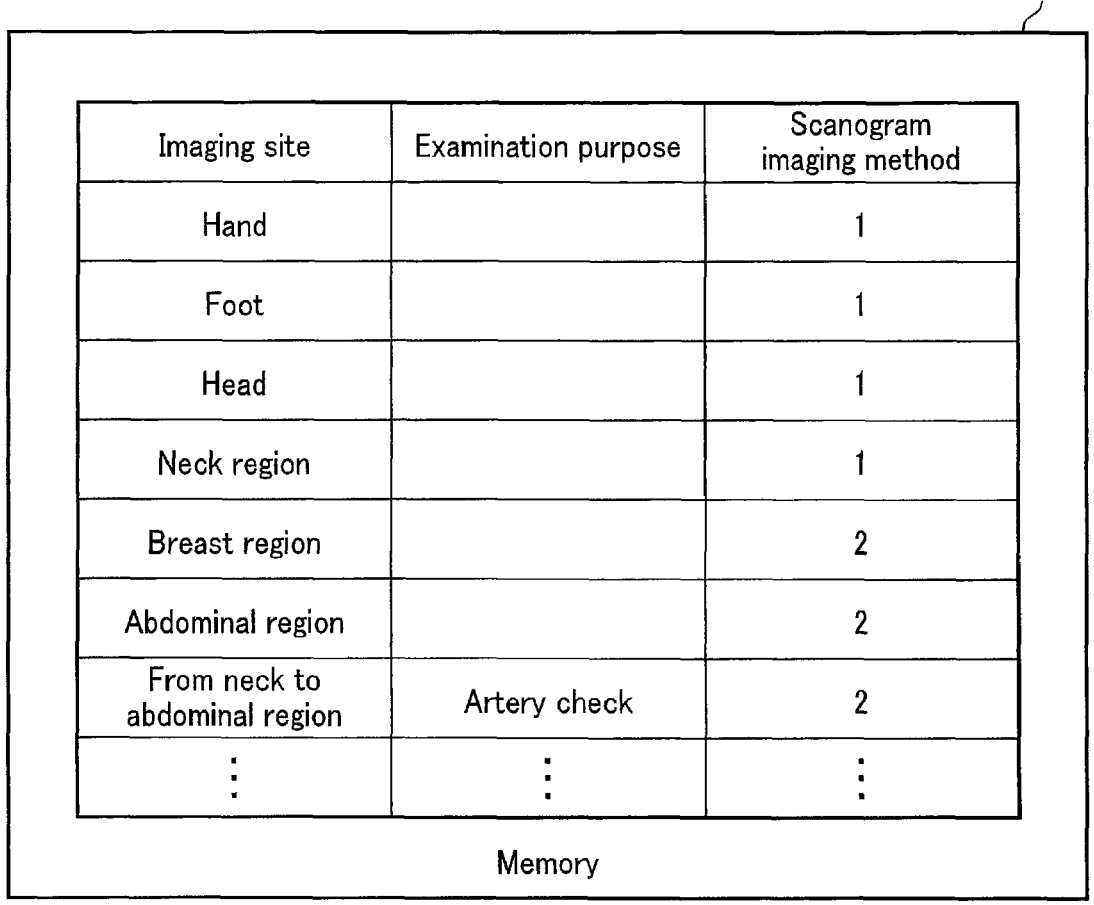
FIG. 13 is a schematic diagram showing one example of table information for use in controlling operations of an X-ray CT apparatus according to an eighth embodiment.

Accordingly, the memory 112 is, in addition to the configuration described above, adapted to store table information for the processing circuitry 116 to determine which of the first scanogram imaging and the second scanogram imaging should be performed. This table information may contain, in the form of a table, information about imaging sites and information about examination purposes which are associated with either first information indicative of the first scanogram imaging and second information indicative of the second scanogram imaging as shown in, for example, FIG. 13. These first information and second information may discretionarily be, for example, any of character strings "First scanogram imaging" and "Second scanogram imaging", numerical information "1" and "2", logical values "FALSE" and "TRUE", and so on. In the case of the logical values, the value "FALSE" can indicate that the scanogram imaging does not require the couch movement. The value "TRUE" can indicate that the scanogram imaging requires the couch movement. FIG. 13 shows the example where the first information and the second information are the numerical information "1" and "2", respectively.

Figure 14:
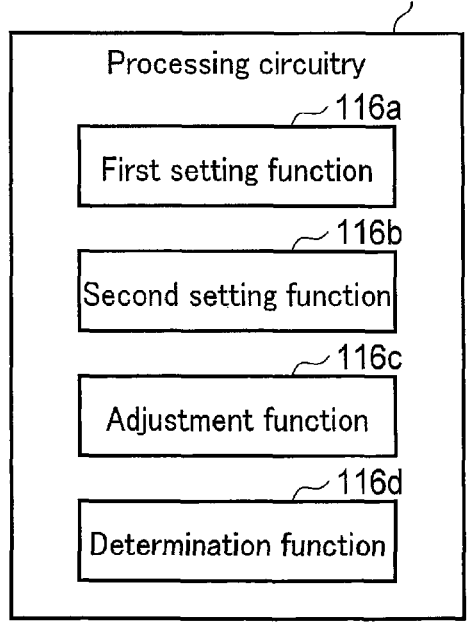
FIG. 14 is a schematic diagram showing an exemplary configuration of processing circuitry according to the eighth embodiment.

Also, the processing circuitry 116 includes, in addition to the configuration described above, a determination function 116d as shown in FIG. 14. The determination function 116d is a function to determine the scanogram imaging method corresponding to either the first scanogram imaging or the second scanogram imaging based on patient information and the table information in the memory 112, in advance of performing the scanogram imaging. With the determination function 116d, the processing circuitry 116 causes the scan controller 110 to proceed with the first scanogram imaging or the second scanogram imaging according to the result of determination.

The remaining aspects may be the same as any of the first to seventh embodiments.

Figure 15:
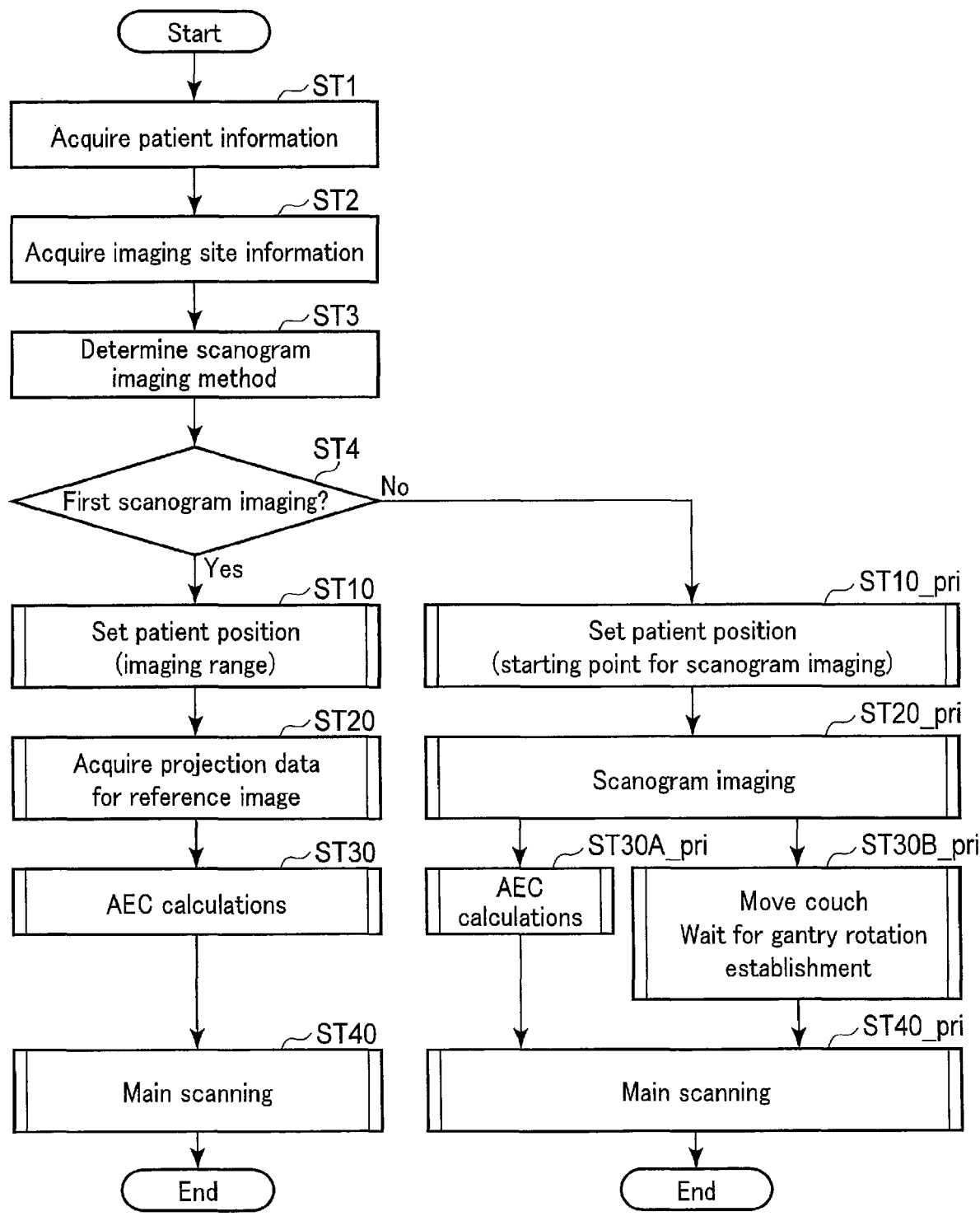
FIG. 15 is a flowchart for explaining an operational sequence of the X-ray CT apparatus according to the eighth embodiment.

Below, operations of the X-ray CT apparatus configured as above will be described with reference to the flowchart of FIG. 15.

In step ST1, the processing circuitry acquires patient information. This is implemented through processing of, for example, receiving an operational input of selecting information for a patient, i.e., examination subject, from the list of scheduled examinations displayed on the display 114, and loading the patient information corresponding to this patient from the memory 112 to a working memory. The patient information may include a patient ID, patient name, date of birth, age, weight, gender, imaging site, examination purpose, etc.

After step ST1, step ST2 is performed where the processing circuitry 116 extracts information including the imaging site and the examination purpose from the patient information loaded to the working memory.

After step ST2, step ST3 is performed where the processing circuitry 116 determines the scanogram imaging method based on the imaging site and/or the examination purpose in the extracted information as well as on the table information in the memory 112.

After step ST3, step ST4 is performed where the processing circuitry 116 identifies if the determined scanogram imaging method is the first scanogram imaging or not. If the scanogram imaging method is identified as the first scanogram imaging, the operation flow advances to step ST10. Subsequently, steps ST10 to ST40 are performed in the manner as described.

On the other hand, if the scanogram imaging method is not identified as the first scanogram imaging in step ST4, the operation flow advances to step ST10_pri for performing the second scanogram imaging. Then, steps ST10_pri to ST40_pri are performed in the manner as described.

According to the eighth embodiment as described above, an advantage of allowing the scanogram imaging suitable for an imaging site, examination purpose, etc. to be performed can be attained in addition to the effects and advantages as in the first to seventh embodiments. For example, if the imaging site is a hand, a foot, a head, or a neck region, the imaging range may not have to be so large, and therefore, the first scanogram imaging is performed so that the scanogram imaging can be done in a shorter time as explained above. Also, since the rotary frame is already rotated when the scanogram imaging is performed, the time to establish rotation of the rotary frame is not required between the scanogram imaging and the main scanning operation, and therefore, the total time of the series of examination procedures can be shortened. If, differently from above, the imaging site is a breast region or an abdominal region, for example, or the examination purpose is to check arteries (when the imaging site takes up the area from the neck to the abdominal region), such an imaging site is large, and accordingly, the second scanogram imaging involving the movement of the couch unit 111 is performed.

Note that which scanogram imaging method should be used for what imaging site or what examination purpose is dependent on the specification of the X-ray CT apparatus employed (in particular, the size of the detection plane of the X-ray detector 103), so this is preset for each apparatus. It is thus possible that some X-ray CT apparatuses may use the first scanogram imaging for a breast region or an abdominal region, instead of the second scanogram imaging as discussed for the above example.

In the instance where multiple imaging sites are imaged sequentially or at once, the processing circuitry 116 determines whether to use the first scanogram imaging or the second scanogram imaging by taking into account the whole scanning range. For one implementation of this determination, for example, the table in the memory 112 may be set with information about a group of typical imaging sites and the scanogram imaging methods for the respective imaging sites in advance, so that the appropriate scanogram imaging method can be easily determined. Also for example, processing steps for the processing circuitry 116 to refer to information about the typical sizes of the respective imaging sites and to then determine the appropriate scanogram imaging method based on such sizes may be stipulated in advance, so that the scanogram imaging method that would suit the actual situation can be determined without the need of using the table.

The description of the eighth embodiment has assumed that the second scanogram imaging that involves movement of the couch unit 111 performs its imaging operation without rotating the X-ray tube unit 101, but the second scanogram imaging in the embodiment is not limited to this configuration. For example, the X-ray tube unit 101 may be rotated, and the scanogram imaging may be performed in multiple, particular directions such as the 0° and 90° directions during the rotation, or the helical scanning may be performed. Such a scanogram imaging method may also be reserved as one option that can be determined according to the table associating with an imaging site, examination purpose, etc., so that the embodiment can realize the scanogram imaging methods suitably prepared for various examinations while contributing to the reduction of imaging operation times.

Additionally, there might be the instances where the scanogram imaging that should be performed cannot be determined from an imaging site or an examination purpose, or the instances where the typical determination criteria are not applicable. To deal with such instances, for example, a configuration may be adopted particularly for specific imaging sites or examination purposes, so that the scanogram imaging method that has been once determined in step ST3 is permitted to be changed by a user input, etc. via the operating portion. In this configuration, more concretely, the processing circuitry 116 may cause the display 114 to display, before the scanogram imaging is performed, the name or the like of the determined scanogram imaging method together with a button, etc. for accepting user's approval or non-approval, and conclusively set the scanogram imaging method to be actually performed in response to the operational input on this button, etc. This can prevent inappropriate scanogram imaging from being performed.

In another exemplary configuration, the user, etc. may be prompted to set the scanogram imaging method for specific imaging sites or examination purposes, without having the table prestore applicable scanogram imaging methods. More concretely, and for example, the processing circuitry 116 may cause the display 114 to display, in step ST3, a message window prompting the user, etc. to make an operational input for selecting which scanogram imaging should be performed. As a matter of course, it is possible to prompt and allow the user, etc. to set the scanogram imaging method in also the cases where multiple, specific imaging sites are collectively selected and the scanogram imaging cannot be decided in step ST3 due to the absence of information about such an imaging site group in the table. For example, the processing circuitry 116 may cause the display 114 to display a screen prompting the user, etc. to input for the scanogram imaging method, and decide the scanogram imaging method according to the input given. With these configurations, the same effects and advantages as in the eighth embodiment can be attained while the table is omitted.

The description of the foregoing examples has assumed that the scanogram imaging methods are directly associated with imaging sites and examination purposes by means of the table, but this is not a limitation. For example, the information about the scanogram imaging methods may be incorporated into the patient information so that the scanogram imaging methods are indirectly associated with imaging sites and examination purposes within the patient information. With these configurations, the same effects and advantages as in the eighth embodiment can be attained while the table, and also the input operations for the scanogram imaging methods are omitted.

Ninth Embodiment

The ninth embodiment may be understood as a modification of the first to eighth embodiments, and it adopts a configuration where the normal scanogram imaging (second scanogram imaging) can be performed after the scanogram imaging without the movement of the couch unit 111 is performed.

In terms of the theoretical possibility, when the scanogram imaging without the couch movement as in the foregoing embodiments is performed to image an organ, e.g., a liver, this liver might not be properly covered by the imaged range due to organ abnormalities, etc. Such instances could require processing for the second scanogram imaging, i.e., the normal scanogram imaging, to be additionally performed. To cope with this, the processing circuitry 116 is adapted to enable redo of scanogram imaging.

Figure 16:
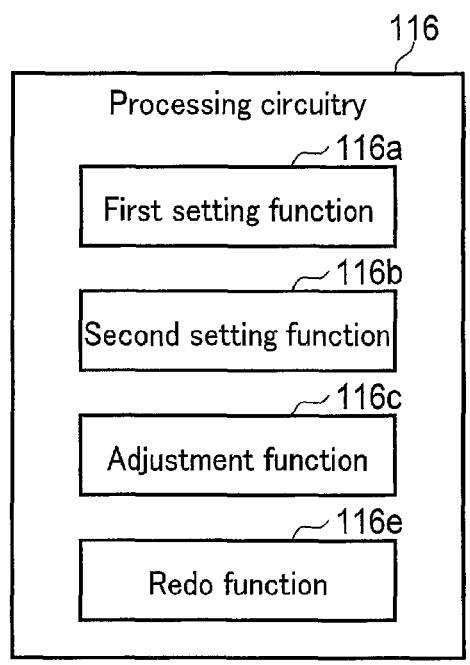
FIG. 16 is a schematic diagram showing an exemplary configuration of processing circuitry according to a ninth embodiment.

For example, the processing circuitry 116 includes, in addition to the configuration described above, a redo function 116e as shown in FIG. 16. With the redo function 116e, the processing circuitry 116 causes, before the main scanning operation, the display 114 to display the reference image obtained from the performed scanogram imaging and an execution button, etc. for inputting an instruction to perform scanogram imaging again. With the redo function 116e, the processing circuitry 116 also causes the scan controller 110 to proceed with one more scanogram imaging according to the operation on the execution button, etc. Note that this one more scanogram imaging may be the scanogram imaging method corresponding to either the first scanogram imaging or the second scanogram imaging, and such a scanogram imaging method may be preset in association with the execution button.

The remaining aspects may be the same as any of the first to eighth embodiments.

Figure 17:
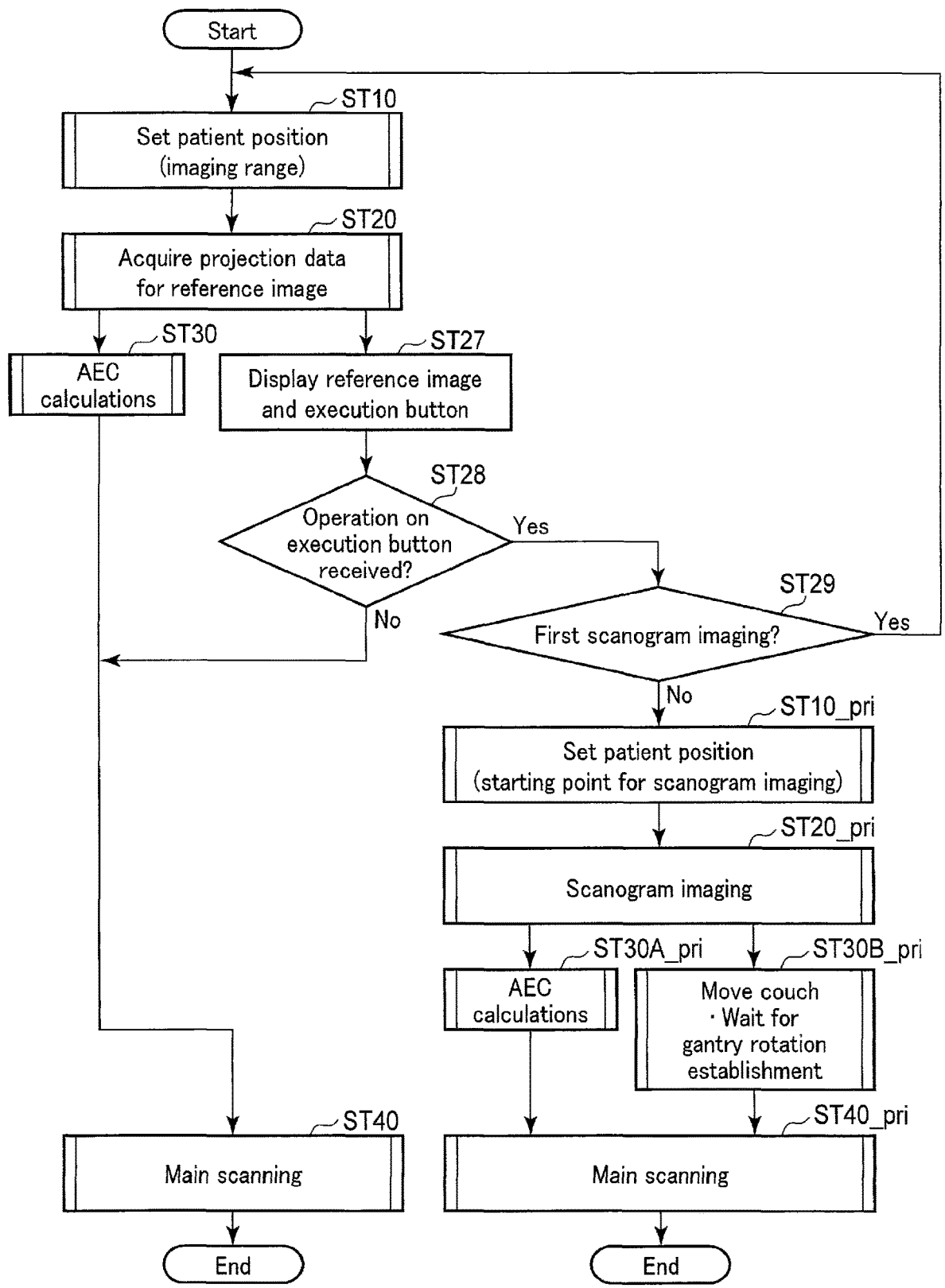
FIG. 17 is a flowchart for explaining an operational sequence of the X-ray CT apparatus according to the ninth embodiment.

Below, operations of the X-ray CT apparatus configured as above will be described with reference to the flowchart of FIG. 17.

Suppose that steps ST10 to ST20 have been performed in the manner as described so that the reference image is generated in step ST20. Steps ST27 to ST29 are then performed after step ST20, and before step ST40. Here, steps ST27 to ST29 may be performed before, after, or in parallel with step ST30. The description will assume an exemplary instance where steps ST27 to ST29 are performed in parallel with step ST30.

In step ST27 after step ST20, the processing circuitry 116 causes the display 114 to display the reference image together with the execution button, etc. for inputting an instruction to perform scanogram imaging again. At this time, if the preceding scanogram imaging was the first scanogram imaging, the processing circuitry 116 assumes that the next scanogram imaging would likely be the second scanogram imaging, and presets the second scanogram imaging. This presetting, as a matter of course, may be discretionarily changed by the user, etc. Meanwhile, step ST30 is performed as background processing.

After step ST27, step ST28 is performed where the processing circuitry 116 judges whether or not an operation on the execution button has been received. If it is judged in step ST28 that an operation on the execution button has been received, the processing circuitry 116 causes the scan controller 110 to proceed with one more scanogram imaging according to the set scanogram imaging method. For example, the processing circuitry 116 judges whether or not the set scanogram imaging method is the first scanogram imaging (step ST29), and if it is judged to be the first scanogram imaging, the operation flow returns to step ST10 and follows the subsequent operational steps. If the judgment in step ST29 indicates that the set scanogram imaging method is not the first scanogram imaging (that is, it is the second scanogram imaging), the operation flow advances to step ST10_pri so that steps ST10_pri to ST40_pri are performed.

In step ST28, on the other hand, if it is judged that an operation on the execution button has not been received, the operation flow advances to step ST40, and step ST40 is performed in the manner as described.

According to the ninth embodiment as described above, an advantage of enabling scanogram imaging to be easily done again can be attained in addition to the effects and advantages as in the first to eighth embodiments.

The first to ninth embodiments have been described, and it is additionally noted that these embodiments, in particular the sixth embodiment, may adopt a configuration where the X-ray CT apparatus performs scanogram imaging that uses low-dose half scanning or full scanning without moving the couch unit 111 as appropriate.

According to at least one embodiment set forth above, cone beam-shaped X-rays are radiated and detected after having passed through a subject, and the reference image of a subject is generated based on the output from the area detector (X-ray detector 103) that is given in response to the radiation of the X-rays from the predetermined position around the rotational axis for a period required to perform the on/off control of the radiation. Imaging conditions for use in the scanning are set based on the generated reference image. The scanning is then controlled based on the set imaging conditions.

Therefore, the reference image for setting imaging conditions and reconstruction conditions can be obtained without a couch movement, and the operation time can be shortened even in the instances of independently obtaining multiple reference images in multiple directions. Moreover, the setup time up to the scanning can also be shortened. Note that, by way of example, the description has assumed the instances where the X-ray CT apparatus according to the respective embodiment relates to obtaining scanograms, but the embodiments are not limited to such scanogram-obtaining techniques. As long as the combination of a preceding operational step of performing X-ray irradiation for acquiring data for a reference image and a subsequent operational step of performing scanning under the scanning conditions determined based on the reference image is adopted, the data acquisition in the preceding operational step is not limited to the purpose of obtaining scanograms, and the data acquisition may be intended for other purposes.

The term "processor" used herein refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (FPGA)), and so on. The processor reads programs stored in the memory and executes them to realize the respective functions. The programs may be incorporated directly in circuits of the processor, instead of being stored in the memory. According to such implementation, the processor reads the programs incorporated in its circuits and executes them to realize the functions. The embodiments herein do not limit the processor to a single circuitry-type processor. A plurality of independent circuits may be combined and integrated as one processor to realize the intended functions. Furthermore, multiple components or features as given in FIG. 1 may be integrated as one processor to realize their functions.

Note that the X-ray tube unit 101 in certain embodiments is one example of an X-ray tube. The X-ray detector 103 in certain embodiments is one example of an area detector. The rotary frame 102 in certain embodiments is one example of a rotary frame. The image processing circuitry 113 in certain embodiments is one example of a generation circuitry. The first setting function 116a, the second setting function 116b, and the adjustment function 116c together constitute one example of processing circuitry. The scan controller 110 in certain embodiments is one example of a controller. The controller may also be called control circuitry.

While certain embodiments have been described, they have been presented by way of example only, and they are not intended to limit the scope of the inventions. These embodiments may be implemented in a variety of other forms with various omissions, substitutions, and changes without departing from the spirit of the inventions. The embodiments and their modifications are covered by the accompanying claims and their equivalents, as would fall within the scope and the gist of the inventions.

The invention claimed is:

1. An X-ray computed tomography (CT) apparatus, comprising:
a couch configured to support a couch top for placement of a subject in such a manner that the couch top is movable;
an X-ray tube configured to radiate cone beam-shaped X-rays;
an area detector configured to detect the X-rays having radiated from the X-ray tube and passed through the subject;
a rotary frame supporting the X-ray tube and the area detector in such a manner that the X-ray tube and the area detector are rotatable about a rotational axis;
generation circuitry configured to generate a reference image of the subject based on an output from the area detector that is given in response to radiation, while the couch top and the rotary frame are stopped, of pulsed X-rays from a predetermined position around the rotational axis;
processing circuitry configured to set, based on the reference image, an imaging condition for scanning the subject; and
a controller configured to control the scanning based on the set imaging condition.

2. The X-ray CT apparatus according to claim 1, wherein the controller is further configured to perform control so that the radiation of the X-rays is suspended and rotation of the rotary frame is continued for a period after completion of X-ray irradiation to generate the reference image and until a start of the scanning.

3. The X-ray CT apparatus according to claim 1, wherein the processing circuitry is further configured to set an imaging range for the subject using an area projector in advance of the scanning.

4. The X-ray CT apparatus according to claim 1, wherein the controller is further configured to control the X-ray tube to radiate the X-rays using, as the predetermined position, either a 0° position at a top of a trajectory around the rotational axis or a 180° position at a bottom of the trajectory, whichever is closer to a position of the X-ray tube around the rotational axis when an instruction to start taking the reference image is given.

5. The X-ray CT apparatus according to claim 1, wherein the controller is further configured to control the X-ray tube to radiate the X-rays using, as the predetermined position, either a 90° position or a 270° position at a respective midpoint between a top and a bottom of a trajectory around the rotational axis, whichever is closer to a position of the X-ray tube around the rotational axis when an instruction to start taking the reference image is given.

6. The X-ray CT apparatus according to claim 1, wherein the processing circuitry is further configured to adjust an imaging range for the scanning using the reference image.

7. The X-ray CT apparatus according to claim 1, wherein the scanning comprises helical scanning.

8. The X-ray CT apparatus according to claim 1, wherein the generation circuitry is further configured to generate the reference image based on an output from the area detector given in response to radiation of the X-rays from the predetermined position during rotation of the rotary frame.

9. The X-ray CT apparatus according to claim 1, wherein the processing circuitry is further configured to determine, before the radiation of the pulsed X-rays and based on at least one of an imaging site and an examination purpose, whether to perform first scanogram imaging to acquire the reference image with the couch top stopped or second scanogram imaging to acquire the reference image with the couch top moving.

10. The X-ray CT apparatus according to claim 9, wherein the processing circuitry is further configured to perform a redo process to cause the second scanogram imaging to be additionally performed, when the imaging site in the reference image acquired by the first scanogram imaging is not covered by an imaged range.

11. The X-ray CT apparatus according to claim 10, wherein the redo process performed by the processing circuitry comprises causing a display to display the reference image acquired by the first scanogram imaging and display an execution button for inputting an instruction to perform the second scanogram imaging.

12. An X-ray CT apparatus, comprising:
   a couch configured to support a couch top for placement of a subject in such a manner that the couch top is movable;
   an X-ray tube configured to radiate cone beam-shaped X-rays;
   an area detector configured to detect the X-rays having radiated from the X-ray tube and passed through the subject;
   a rotary frame supporting the X-ray tube and the area detector in such a manner that the X-ray tube and the area detector are rotatable about a rotational axis;
   generation circuitry configured to generate a reference image of the subject based on an output from the area detector that is given in response to radiation, while the couch top and the rotary frame are stopped, of the X-rays from a predetermined position around the rotational axis for a period that allows for obtaining one fluoroscopic image;
   processing circuitry configured to set, based on the reference image, an imaging condition for use in scanning for the subject; and
   a controller configured to control the scanning based on the set imaging condition.

13. An X-ray CT apparatus, comprising:
   a couch configured to support a couch top for placement of a subject in such a manner that the couch top is movable;
   an X-ray tube configured to radiate cone beam-shaped X-rays;
   an area detector configured to detect the X-rays having radiated from the X-ray tube and passed through the subject;
   a rotary frame supporting the X-ray tube and the area detector in such a manner that the X-ray tube and the area detector are rotatable about a rotational axis;
   generation circuitry configured to generate a reference image of the subject based on an output from the area detector that is given in response to radiation, while the couch top and the rotary frame are stopped, of the X-rays from a predetermined position around the rotational axis for a period corresponding to one or more views;
   processing circuitry configured to set, based on the reference image, an imaging condition for use in scanning for the subject; and
   a controller configured to control the scanning based on the set imaging condition.

14. An imaging control method performed by an X-ray CT apparatus comprising a couch configured to support a couch top for placement of a subject in such a manner that the couch top is movable, an X-ray tube for radiating cone beam-shaped X-rays, an area detector for detecting the X-rays having radiated from the X-ray tube and passed through the subject, and a rotary frame supporting the X-ray tube and the area detector in such a manner that the X-ray tube and the area detector are rotatable about a rotational axis, the method comprising:
   initiating rotation of the rotary frame;
   generating a reference image of the subject based on an output from the area detector that is given in response to radiation, while the couch top and the rotary frame are stopped, of the X-rays from a predetermined position around the rotational axis for a period corresponding to one or more views;
   setting, based on the reference image, an imaging condition for scanning for the subject; and
   controlling the scanning based on the set imaging condition.

* * * * *